US010299790B2

(12) United States Patent
Beardsley

(10) Patent No.: US 10,299,790 B2
(45) Date of Patent: May 28, 2019

(54) ADAPTER WITH CENTERING MECHANISM FOR ARTICULATION JOINT

(71) Applicant: Covidien LP, Mansfield, MA (US)

(72) Inventor: John Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 259 days.

(21) Appl. No.: 15/449,210

(22) Filed: Mar. 3, 2017

(65) Prior Publication Data
US 2018/0250005 A1 Sep. 6, 2018

(51) Int. Cl.
*A61B 17/00* (2006.01)
*A61B 17/072* (2006.01)
*F16C 11/06* (2006.01)
*A61B 17/29* (2006.01)
(Continued)

(52) U.S. Cl.
CPC ........ *A61B 17/07207* (2013.01); *F16C 11/06* (2013.01); *A61B 2017/0046* (2013.01); *A61B 2017/0069* (2013.01); *A61B 2017/00115* (2013.01); *A61B 2017/00323* (2013.01); *A61B 2017/00398* (2013.01); *A61B 2017/00473* (2013.01); *A61B 2017/00477* (2013.01); *A61B 2017/00734* (2013.01); *A61B 2017/07257* (2013.01); *A61B 2017/07271* (2013.01); *A61B 2017/2927* (2013.01); *A61B 2090/035* (2016.02); *A61B 2090/0811* (2016.02); *F16H 19/003* (2013.01)

(58) Field of Classification Search
CPC . A61B 17/00; A61B 17/072; A61B 17/07207; F16C 11/06; F16C 11/0652; Y10T 403/32032; Y10T 403/32041; Y10T 403/32688
See application file for complete search history.

(56) References Cited

U.S. PATENT DOCUMENTS

| | | | |
|---|---|---|---|
| 2,777,340 A | 1/1957 | Hettwer et al. | |
| 2,957,353 A | 10/1960 | Babacz | |
| 3,079,606 A | 3/1963 | Bobrov et al. | |

(Continued)

FOREIGN PATENT DOCUMENTS

| | | |
|---|---|---|
| AU | 198654765 | 9/1986 |
| AU | 2008229795 A1 | 4/2009 |

(Continued)

OTHER PUBLICATIONS

U.S. Appl. No. 15/460,361, filed Mar. 16, 2017, inventor, John Beardsley.

(Continued)

*Primary Examiner* — Daniel J Wiley

(57) ABSTRACT

A joint assembly of an adapter defines a first longitudinal axis and includes first and second hinges, first and second rings, a joint cover, and a biasing mechanism. The joint cover has first and second cover portions. The first ring is pivotally coupled to the first hinge and the first cover portion is pivotally coupled to the first hinge to define a first joint center. The second ring is pivotally coupled to the second cover portion and the second hinge is pivotally coupled to the second ring to define a second joint center that is spaced from the first joint center. The first and second joint centers define a cover axis of the joint cover. The biasing mechanism is engaged with the first ring and the joint cover to bias the joint cover towards an aligned configuration in which the cover axis is aligned with the first longitudinal axis.

19 Claims, 19 Drawing Sheets

(51) Int. Cl.
  *A61B 90/00* (2016.01)
  *F16H 19/00* (2006.01)

(56) References Cited

U.S. PATENT DOCUMENTS

| | | |
|---|---|---|
| 3,111,328 A | 11/1963 | Di Rito et al. |
| 3,490,675 A | 1/1970 | Green et al. |
| 3,499,591 A | 3/1970 | Green |
| 3,695,058 A | 10/1972 | Keith, Jr. |
| 3,734,515 A | 5/1973 | Dudek |
| 3,759,336 A | 9/1973 | Marcovitz et al. |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,162,399 A | 7/1979 | Hudson |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,606,343 A | 8/1986 | Conta et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,705,038 A | 11/1987 | Sjostrom et al. |
| 4,722,685 A | 2/1988 | de Estrada et al. |
| 4,728,020 A | 3/1988 | Green et al. |
| 4,752,024 A | 6/1988 | Green et al. |
| 4,784,137 A | 11/1988 | Kulik et al. |
| 4,823,807 A | 4/1989 | Russell et al. |
| 4,863,088 A | 9/1989 | Redmond et al. |
| 4,869,415 A | 9/1989 | Fox |
| 4,874,181 A | 10/1989 | Hsu |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,118 A | 7/1992 | Walmesley |
| 5,129,570 A | 7/1992 | Schulze et al. |
| 5,141,144 A | 8/1992 | Foslien et al. |
| 5,152,744 A | 10/1992 | Krause et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,301,061 A | 4/1994 | Nakada et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,350,355 A | 9/1994 | Sklar |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,400,267 A | 3/1995 | Denen et al. |
| 5,403,312 A | 4/1995 | Yates et al. |
| 5,405,072 A | 4/1995 | Zlock et al. |
| 5,407,293 A | 4/1995 | Crainich |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,427,087 A | 6/1995 | Ito et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,476,379 A | 12/1995 | Disel |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |

(56) References Cited

U.S. PATENT DOCUMENTS

| | | |
|---|---|---|
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,609,560 A | 3/1997 | Ichikawa et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,762,603 A | 6/1998 | Thompson |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,792,573 A | 8/1998 | Pitzen et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,863,159 A | 1/1999 | Lasko |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,908,427 A | 6/1999 | McKean et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 5,993,454 A | 11/1999 | Longo |
| 6,004,335 A | 12/1999 | Vaitekunas et al. |
| 6,010,054 A | 1/2000 | Johnson et al. |
| 6,013,991 A | 1/2000 | Philipp |
| 6,017,354 A | 1/2000 | Culp et al. |
| 6,032,849 A | 3/2000 | Mastri et al. |
| 6,045,560 A | 4/2000 | McKean et al. |

(56) References Cited

U.S. PATENT DOCUMENTS

| | | |
|---|---|---|
| 6,063,097 A | 5/2000 | Oi et al. |
| 6,079,606 A | 6/2000 | Milliman et al. |
| 6,090,123 A | 7/2000 | Culp et al. |
| 6,099,551 A | 8/2000 | Gabbay |
| 6,109,500 A | 8/2000 | Alli et al. |
| 6,126,651 A | 10/2000 | Mayer |
| 6,129,547 A | 10/2000 | Cise et al. |
| 6,131,789 A | 10/2000 | Schulze et al. |
| 6,131,790 A | 10/2000 | Piraka |
| 6,155,473 A | 12/2000 | Tompkins et al. |
| 6,165,169 A | 12/2000 | Panescu et al. |
| 6,197,017 B1 | 3/2001 | Brock et al. |
| 6,202,914 B1 | 3/2001 | Geiste et al. |
| 6,239,732 B1 | 5/2001 | Cusey |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,302,311 B1 | 10/2001 | Adams et al. |
| 6,315,183 B1 | 11/2001 | Piraka |
| 6,315,184 B1 | 11/2001 | Whitman |
| 6,321,855 B1 | 11/2001 | Barnes |
| 6,325,810 B1 | 12/2001 | Hamilton et al. |
| 6,329,778 B1 | 12/2001 | Culp et al. |
| 6,330,965 B1 | 12/2001 | Milliman et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,391,038 B2 | 5/2002 | Vargas et al. |
| 6,398,797 B2 | 6/2002 | Bombard et al. |
| 6,434,507 B1 | 8/2002 | Clayton et al. |
| 6,436,097 B1 | 8/2002 | Nardella |
| 6,439,446 B1 | 8/2002 | Perry et al. |
| 6,443,973 B1 | 9/2002 | Whitman |
| 6,461,372 B1 | 10/2002 | Jensen et al. |
| 6,478,804 B2 | 11/2002 | Vargas et al. |
| 6,488,196 B1 | 12/2002 | Fenton, Jr. |
| 6,488,197 B1 | 12/2002 | Whitman |
| 6,491,201 B1 | 12/2002 | Whitman |
| 6,503,257 B2 | 1/2003 | Grant et al. |
| 6,505,768 B2 | 1/2003 | Whitman |
| 6,533,157 B1 | 3/2003 | Whitman |
| 6,537,280 B2 | 3/2003 | Dinger et al. |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,610,066 B2 | 8/2003 | Dinger et al. |
| 6,611,793 B1 | 8/2003 | Burnside et al. |
| 6,619,529 B2 | 9/2003 | Green et al. |
| D480,808 S | 10/2003 | Wells et al. |
| 6,644,532 B2 | 11/2003 | Green et al. |
| 6,645,218 B1 | 11/2003 | Cassidy et al. |
| 6,654,999 B2 | 12/2003 | Stoddard et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,699,177 B1 | 3/2004 | Wang et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,743,240 B2 | 6/2004 | Smith et al. |
| 6,755,338 B2 | 6/2004 | Hahnen et al. |
| 6,783,524 B2 | 8/2004 | Anderson et al. |
| 6,783,533 B2 | 8/2004 | Green et al. |
| 6,786,382 B1 | 9/2004 | Hoffman |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,860,892 B1 | 3/2005 | Tanaka et al. |
| 6,877,647 B2 | 4/2005 | Green et al. |
| 6,889,116 B2 | 5/2005 | Jinno |
| 6,899,538 B2 | 5/2005 | Matoba |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| RE39,152 E | 6/2006 | Aust et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,021 B1 | 7/2007 | Johnson |
| 7,238,195 B2 | 7/2007 | Viola |
| 7,246,734 B2 | 7/2007 | Shelton, IV |
| 7,252,660 B2 | 8/2007 | Kunz |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |

(56) References Cited

U.S. PATENT DOCUMENTS

| | | |
|---|---|---|
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,549,564 B2 | 6/2009 | Boudreaux |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,699,835 B2 | 4/2010 | Lee et al. |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,758,613 B2 | 7/2010 | Whitman |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |

(56) References Cited

U.S. PATENT DOCUMENTS

| | | |
|---|---|---|
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,822,458 B2 | 10/2010 | Webster, III et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,905,897 B2 | 3/2011 | Whitman et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,922,719 B2 | 4/2011 | Ralph et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,947,034 B2 | 5/2011 | Whitman |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,035,487 B2 | 10/2011 | Malackowski |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |

(56) References Cited

U.S. PATENT DOCUMENTS

| | | |
|---|---|---|
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,114,118 B2 | 2/2012 | Knodel et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,152,516 B2 | 4/2012 | Harvey et al. |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,182,494 B1 | 5/2012 | Yencho et al. |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,186,587 B2 | 5/2012 | Zmood et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,367 B2 | 7/2012 | Hsu |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,292,888 B2 | 10/2012 | Whitman |
| 8,303,581 B2 | 11/2012 | Arts et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,855 B2 | 1/2013 | Hillely et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,144 B2 | 1/2013 | Whitman et al. |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,633 B2 | 2/2013 | Simaan et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,057 B2 | 2/2013 | Cude et al. |
| 8,381,828 B2 | 2/2013 | Whitman et al. |

(56) References Cited

U.S. PATENT DOCUMENTS

| | | |
|---|---|---|
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,391,957 B2 | 3/2013 | Carlson et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,926 B2 | 3/2013 | Nobis et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,585 B2 | 6/2013 | Whitman |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czemik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,551,076 B2 | 10/2013 | Duval et al. |
| 8,556,151 B2 | 10/2013 | Viola |
| 8,561,870 B2 | 10/2013 | Baxter et al. |
| 8,561,871 B2 | 10/2013 | Rajappa et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,287 B2 | 12/2013 | Yates et al. |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,623,000 B2 | 1/2014 | Humayun et al. |
| 8,627,994 B2 | 1/2014 | Zemlok et al. |
| 8,627,995 B2 | 1/2014 | Smith et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,463 B2 | 1/2014 | Drinan et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |

(56) References Cited

U.S. PATENT DOCUMENTS

| | | |
|---|---|---|
| 8,696,552 B2 | 4/2014 | Whitman |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,715,306 B2 | 5/2014 | Faller et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,858,571 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,905,289 B2 | 12/2014 | Patel et al. |
| 8,919,630 B2 | 12/2014 | Milliman |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,680 B2 | 1/2015 | Milliman |
| 8,931,682 B2 | 1/2015 | Timm et al. |
| 8,931,693 B1 | 1/2015 | Kumar et al. |
| 8,939,344 B2 | 1/2015 | Olson et al. |
| 8,950,646 B2 | 2/2015 | Viola |
| 8,955,732 B2 | 2/2015 | Zemlok et al. |
| 8,958,429 B2 | 2/2015 | Shukla et al. |
| 8,960,517 B2 | 2/2015 | Lee |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,992,422 B2 | 3/2015 | Spivey et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,016,546 B2 | 4/2015 | Demmy et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,033,203 B2 | 5/2015 | Woodard, Jr. et al. |
| 9,033,868 B2 | 5/2015 | Whitman et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,055,943 B2 | 6/2015 | Zemlok et al. |
| 9,060,770 B2 | 6/2015 | Shelton, IV et al. |
| 9,064,653 B2 | 6/2015 | Prest et al. |
| 9,072,515 B2 | 7/2015 | Hall et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,847 B2 | 8/2015 | Whitman et al. |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,875 B2 | 8/2015 | Viola et al. |
| 9,113,876 B2 | 8/2015 | Zemlok et al. |
| 9,113,880 B2 | 8/2015 | Zemlok et al. |
| 9,113,899 B2 | 8/2015 | Garrison et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,961 B2 | 3/2016 | Whitman et al. |
| 9,282,962 B2 | 3/2016 | Schmid et al. |
| 9,282,963 B2 | 3/2016 | Bryant |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |

(56) References Cited

U.S. PATENT DOCUMENTS

| | | |
|---|---|---|
| 9,295,522 B2 | 3/2016 | Kostrzewski |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty |
| 9,386,983 B2 | 7/2016 | Swensgard et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0108357 A1 | 6/2004 | Milliman et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0125027 A1 | 6/2005 | Knodel et al. |
| 2005/0131442 A1 | 6/2005 | Yachia et al. |
| 2005/0216055 A1 | 9/2005 | Scirica et al. |
| 2006/0049229 A1 | 3/2006 | Milliman et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0180634 A1 | 8/2006 | Shelton et al. |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0152014 A1 | 7/2007 | Gillum et al. |
| 2007/0170225 A1 | 7/2007 | Shelton et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0078802 A1 | 4/2008 | Hess et al. |
| 2008/0109012 A1 | 5/2008 | Falco et al. |
| 2008/0110958 A1 | 5/2008 | McKenna et al. |
| 2008/0110961 A1 | 5/2008 | Voegele et al. |
| 2008/0147089 A1 | 6/2008 | Loh et al. |
| 2008/0167736 A1 | 7/2008 | Swayze et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0012533 A1 | 1/2009 | Barbagli et al. |
| 2009/0090763 A1 | 4/2009 | Zemlok et al. |
| 2009/0090766 A1 | 4/2009 | Knodel |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0242610 A1 | 10/2009 | Shelton, IV et al. |
| 2009/0254094 A1 | 10/2009 | Knapp et al. |
| 2009/0255974 A1 | 10/2009 | Viola |
| 2009/0299141 A1 | 12/2009 | Downey et al. |
| 2009/0308907 A1 | 12/2009 | Nalagatla et al. |
| 2010/0012703 A1 | 1/2010 | Calabrese et al. |
| 2010/0023022 A1 | 1/2010 | Zeiner et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0193568 A1 | 8/2010 | Scheib et al. |
| 2010/0211053 A1 | 8/2010 | Ross et al. |
| 2010/0224668 A1 | 9/2010 | Fontayne et al. |
| 2010/0225073 A1 | 9/2010 | Porter et al. |
| 2010/0249802 A1 | 9/2010 | May et al. |
| 2010/0252611 A1 | 10/2010 | Ezzat et al. |

(56) References Cited

U.S. PATENT DOCUMENTS

| | | |
|---|---|---|
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0071508 A1 | 3/2011 | Duval et al. |
| 2011/0077673 A1 | 3/2011 | Grubac et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0147433 A1 | 6/2011 | Shelton, IV et al. |
| 2011/0155783 A1 | 6/2011 | Rajappa et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0278343 A1 | 11/2011 | Knodel et al. |
| 2011/0290854 A1 | 12/2011 | Timm et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074199 A1 | 3/2012 | Olson et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0089131 A1 | 4/2012 | Zemlok et al. |
| 2012/0091183 A1 | 4/2012 | Manoux et al. |
| 2012/0104071 A1 | 5/2012 | Bryant |
| 2012/0116368 A1 | 5/2012 | Viola |
| 2012/0138659 A1 | 6/2012 | Marczyk et al. |
| 2012/0143002 A1 | 6/2012 | Aranyi et al. |
| 2012/0172924 A1 | 7/2012 | Allen, IV |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0245428 A1 | 9/2012 | Smith et al. |
| 2012/0248169 A1 | 10/2012 | Widenhouse et al. |
| 2012/0253326 A1 | 10/2012 | Kleyman |
| 2012/0253329 A1 | 10/2012 | Zemlok et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0093149 A1 | 4/2013 | Saur et al. |
| 2013/0098964 A1 | 4/2013 | Smith et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0178838 A1 | 7/2013 | Malkowski |
| 2013/0181035 A1 | 7/2013 | Milliman |
| 2013/0184704 A1 | 7/2013 | Beardsley et al. |
| 2013/0193188 A1 | 8/2013 | Shelton, IV et al. |
| 2013/0214025 A1 | 8/2013 | Zemlok et al. |
| 2013/0240596 A1 | 9/2013 | Whitman |
| 2013/0256380 A1 | 10/2013 | Schmid et al. |
| 2013/0274722 A1 | 10/2013 | Kostrzewski et al. |
| 2013/0277410 A1 | 10/2013 | Fernandez et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334280 A1 | 12/2013 | Krehel et al. |
| 2013/0334281 A1 | 12/2013 | Williams |
| 2014/0005662 A1 | 1/2014 | Shelton, IV |
| 2014/0012236 A1 | 1/2014 | Williams et al. |
| 2014/0012237 A1 | 1/2014 | Pribanic et al. |
| 2014/0012238 A1 | 1/2014 | Chen et al. |
| 2014/0012289 A1 | 1/2014 | Snow et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0025046 A1 | 1/2014 | Williams et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0110455 A1 | 4/2014 | Ingmanson et al. |
| 2014/0114403 A1 | 4/2014 | Dale et al. |
| 2014/0131419 A1 | 5/2014 | Bettuchi |
| 2014/0138423 A1 | 5/2014 | Whitfield et al. |
| 2014/0144970 A1 | 5/2014 | Aranyi et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0207125 A1 | 7/2014 | Applegate et al. |
| 2014/0207182 A1 | 7/2014 | Zergiebel et al. |
| 2014/0207185 A1 | 7/2014 | Goble et al. |

(56) References Cited

U.S. PATENT DOCUMENTS

| | | |
|---|---|---|
| 2014/0236173 A1 | 8/2014 | Scirica et al. |
| 2014/0236174 A1 | 8/2014 | Williams et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0276932 A1 | 9/2014 | Williams et al. |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0299647 A1 | 10/2014 | Scirica et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0367445 A1 | 12/2014 | Ingmanson et al. |
| 2014/0367446 A1 | 12/2014 | Ingmanson et al. |
| 2014/0373652 A1 | 12/2014 | Zergiebel et al. |
| 2015/0014392 A1 | 1/2015 | Williams et al. |
| 2015/0048143 A1 | 2/2015 | Scheib et al. |
| 2015/0048144 A1 | 2/2015 | Whitman |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0133996 A1 | 5/2015 | Shelton, IV et al. |
| 2015/0134076 A1 | 5/2015 | Shelton, IV et al. |
| 2015/0150547 A1 | 6/2015 | Ingmanson et al. |
| 2015/0150556 A1 | 6/2015 | McCuen |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0201931 A1 | 7/2015 | Zergiebel et al. |
| 2015/0209040 A1 | 7/2015 | Whitman et al. |
| 2015/0250474 A1 | 9/2015 | Abbott et al. |
| 2015/0272577 A1 | 10/2015 | Zemlok et al. |
| 2015/0297199 A1 | 10/2015 | Nicholas et al. |
| 2015/0297225 A1 | 10/2015 | Huitema et al. |
| 2015/0303996 A1 | 10/2015 | Calderoni |
| 2015/0316431 A1 | 11/2015 | Collins et al. |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2015/0374449 A1 | 12/2015 | Chowaniec et al. |
| 2015/0380187 A1 | 12/2015 | Zergiebel et al. |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0095596 A1 | 4/2016 | Scirica et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |

(56) References Cited

U.S. PATENT DOCUMENTS

| | | |
|---|---|---|
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |

FOREIGN PATENT DOCUMENTS

| | | |
|---|---|---|
| CA | 2451558 A1 | 1/2003 |
| CA | 2773414 A1 | 11/2012 |
| CA | 2824590 A1 | 4/2014 |
| CA | 2884962 A1 | 11/2015 |
| CN | 101856251 A | 10/2010 |
| CN | 102247182 A | 11/2011 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| DE | 102008053842 A1 | 5/2010 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A2 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0634144 A1 | 1/1995 |
| EP | 0648476 A1 | 4/1995 |
| EP | 0656188 A2 | 6/1995 |
| EP | 0666057 A2 | 8/1995 |
| EP | 0686374 A2 | 12/1995 |
| EP | 0705571 A1 | 4/1996 |
| EP | 0 760 230 A1 | 3/1997 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1 813 203 A2 | 8/2007 |
| EP | 1813199 A1 | 8/2007 |
| EP | 1813212 A1 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2090253 A2 | 8/2009 |
| EP | 2090254 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2583630 A2 | 4/2013 |
| EP | 2586382 A2 | 5/2013 |
| EP | 2606834 A2 | 6/2013 |
| EP | 2649948 A1 | 10/2013 |
| EP | 2668910 A2 | 12/2013 |
| EP | 2676615 A2 | 12/2013 |
| EP | 2815705 A1 | 12/2014 |
| EP | 2907456 A1 | 8/2015 |
| EP | 2937047 A1 | 10/2015 |
| EP | 3192455 A1 | 7/2017 |
| ES | 2333509 A1 | 2/2010 |
| FR | 391239 A | 10/1908 |
| FR | 2542188 A1 | 9/1984 |
| FR | 2660851 A1 | 10/1991 |
| FR | 2681775 A1 | 4/1993 |
| FR | 2861574 A1 | 5/2005 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51-149985 | 12/1976 |
| JP | 08-038488 | 2/1996 |
| JP | 2001-87272 | 4/2001 |
| JP | 2005-125075 A | 5/2005 |
| KR | 20120022521 A | 3/2012 |
| SU | 659146 A1 | 4/1979 |
| SU | 728848 A1 | 4/1980 |
| SU | 980703 A1 | 12/1982 |
| SU | 990220 A1 | 1/1983 |
| WO | 08302247 | 7/1983 |
| WO | 89/10094 A1 | 11/1989 |
| WO | 9210976 A1 | 7/1992 |
| WO | 9308754 A1 | 5/1993 |

(56) References Cited

FOREIGN PATENT DOCUMENTS

| | | |
|---|---|---|
| WO | 9314706 A1 | 8/1993 |
| WO | 99/15086 A1 | 4/1999 |
| WO | 2000/072760 A1 | 12/2000 |
| WO | 2000/072765 A1 | 12/2000 |
| WO | 2003/000138 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003090630 A2 | 11/2003 |
| WO | 2004/032760 A2 | 4/2004 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/008178 A2 | 1/2008 |
| WO | 2008/020964 A2 | 2/2008 |
| WO | 2008/131362 A2 | 10/2008 |
| WO | 2008/133956 A2 | 11/2008 |
| WO | 2009/039506 A1 | 3/2009 |
| WO | 2007014355 A3 | 4/2009 |
| WO | 2009071070 A2 | 6/2009 |
| WO | 2009091497 A2 | 7/2009 |
| WO | 2009/132359 A2 | 10/2009 |
| WO | 2009/143092 A1 | 11/2009 |
| WO | 2009149234 A1 | 12/2009 |
| WO | 2010/112609 A1 | 10/2010 |
| WO | 2011/108840 A2 | 9/2011 |
| WO | 2012/040984 A1 | 4/2012 |
| WO | 2013166409 A1 | 11/2013 |
| WO | 20150191887 A1 | 12/2015 |

OTHER PUBLICATIONS

U.S. Appl. No. 15/397,240, filed Jan. 3, 2017, inventor David Nicholas.
European Search Report dated Aug. 13, 2018 in European Appln. No. 18159310.

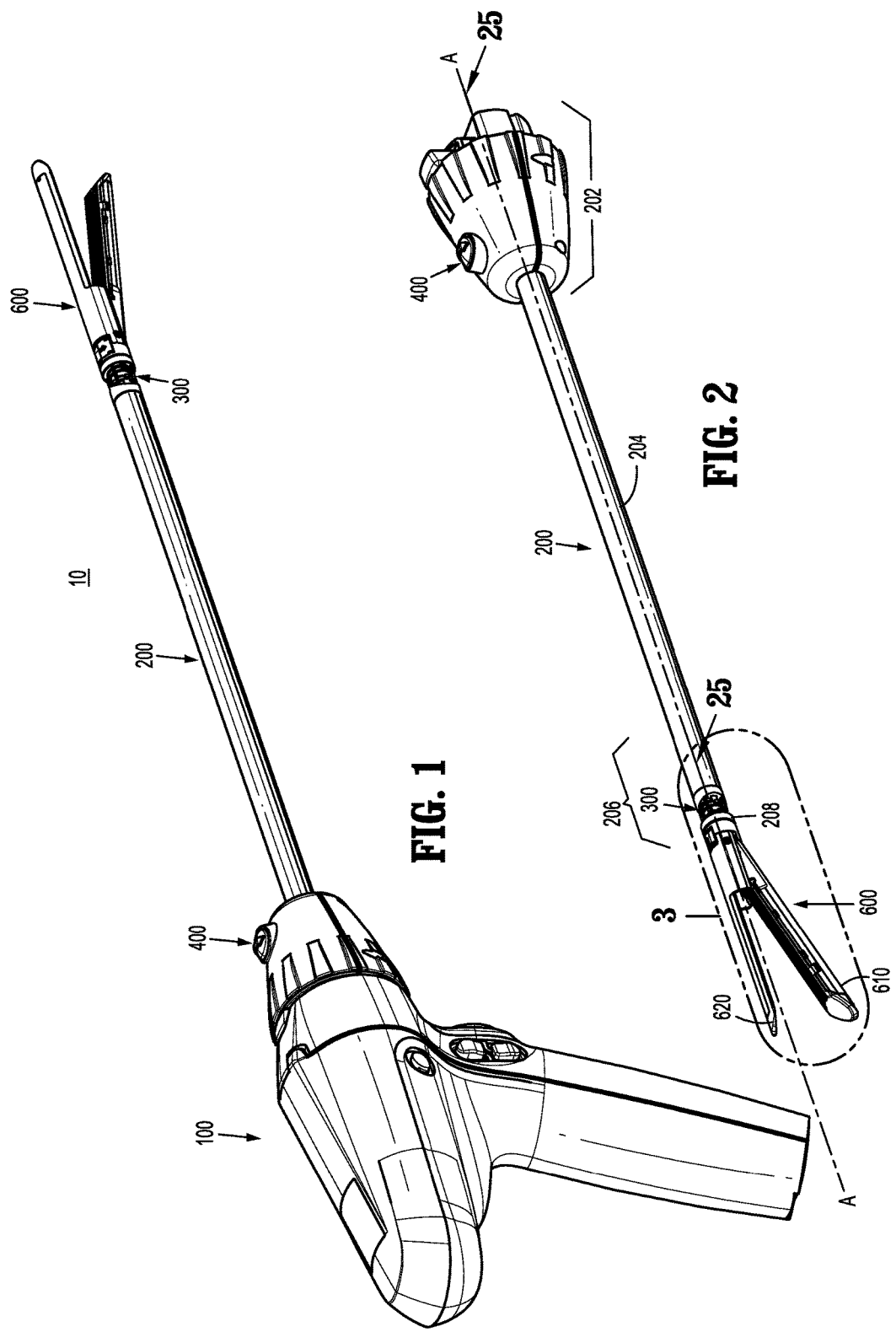

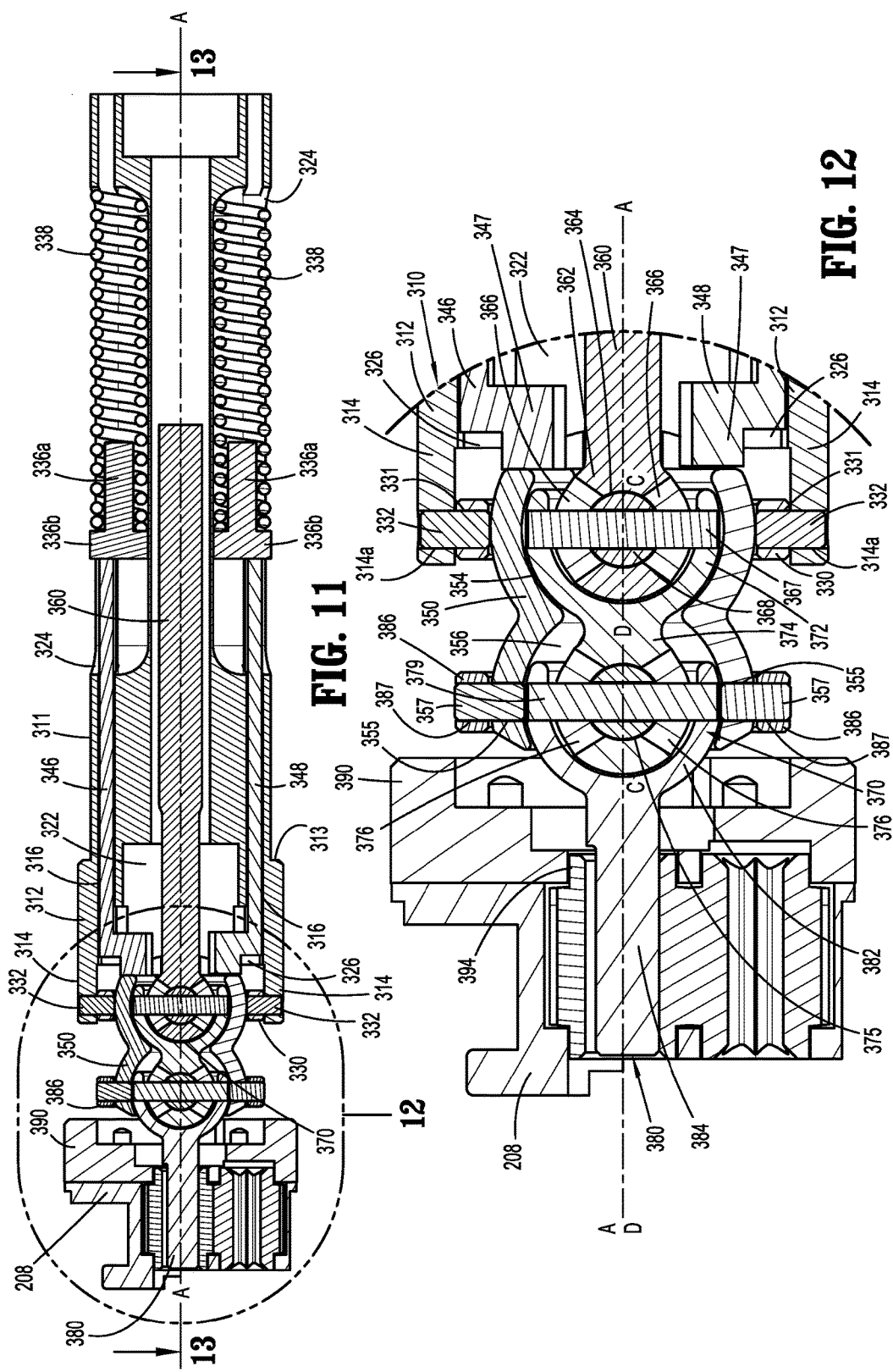

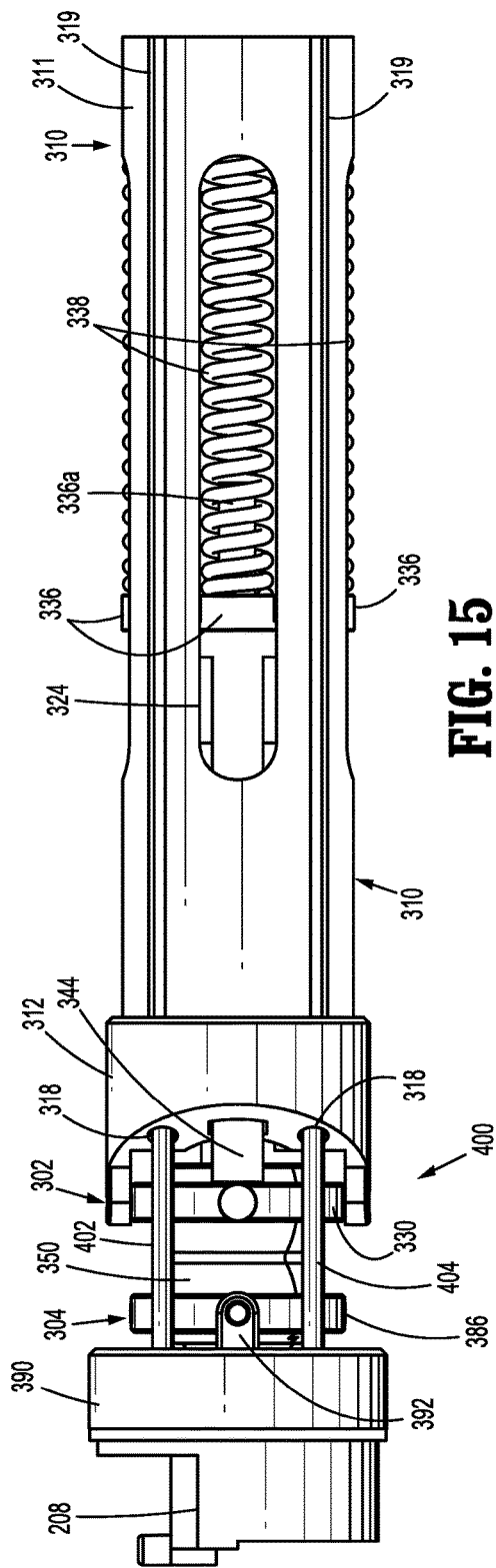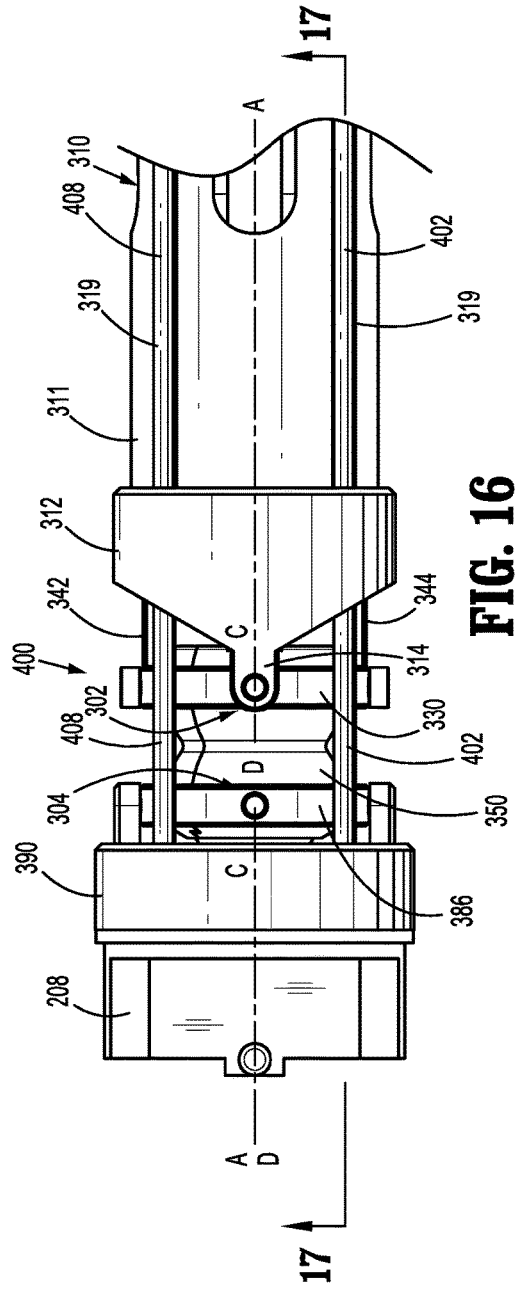
FIG. 15
FIG. 16

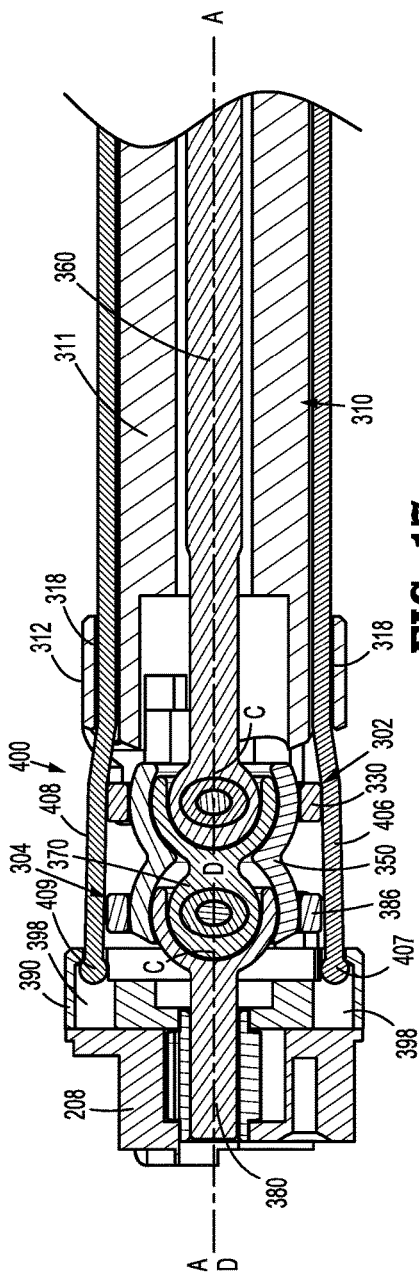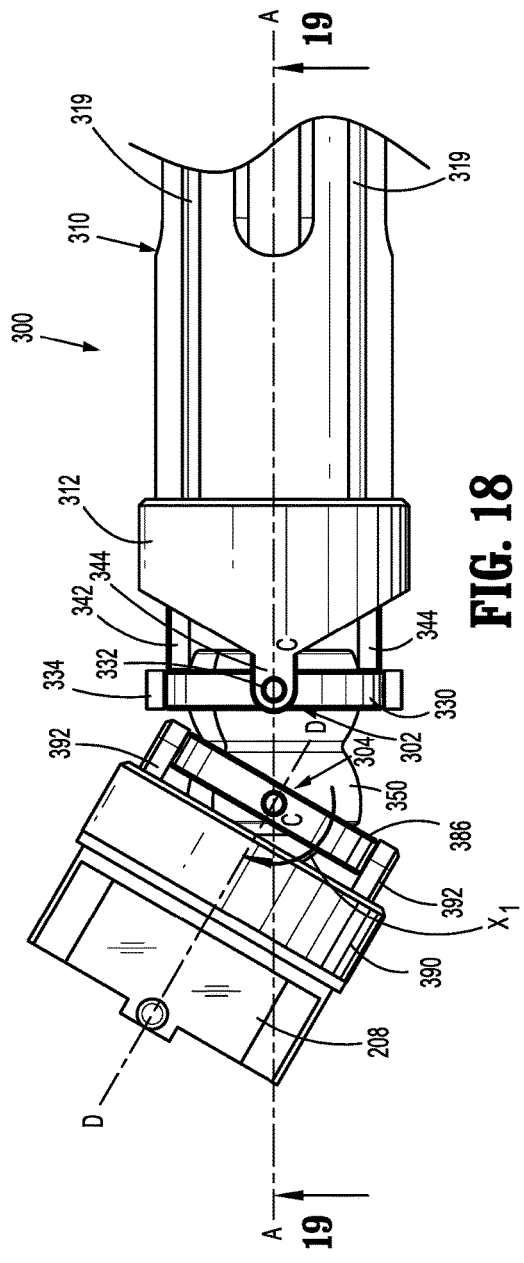

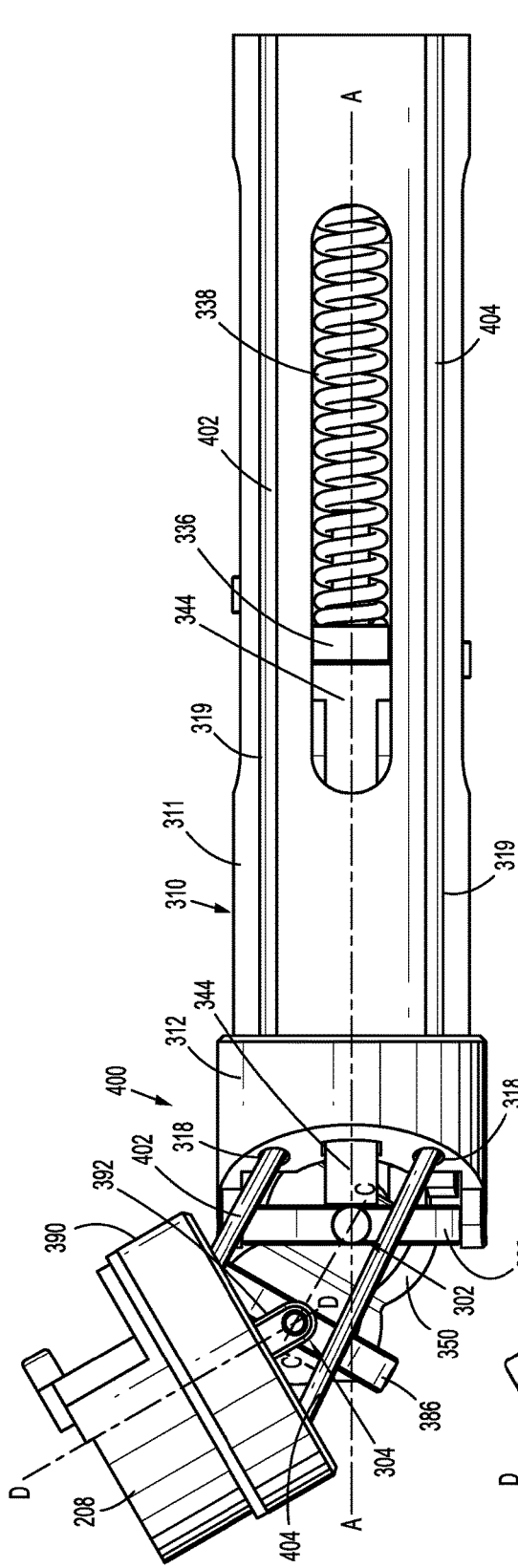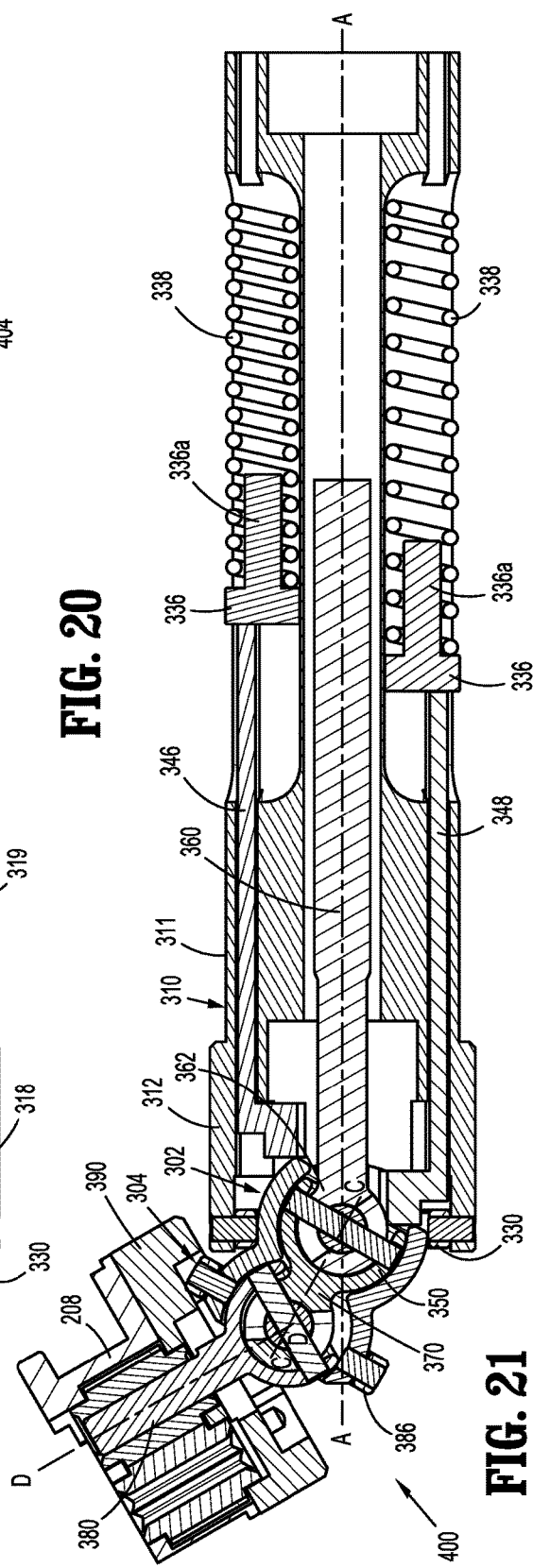

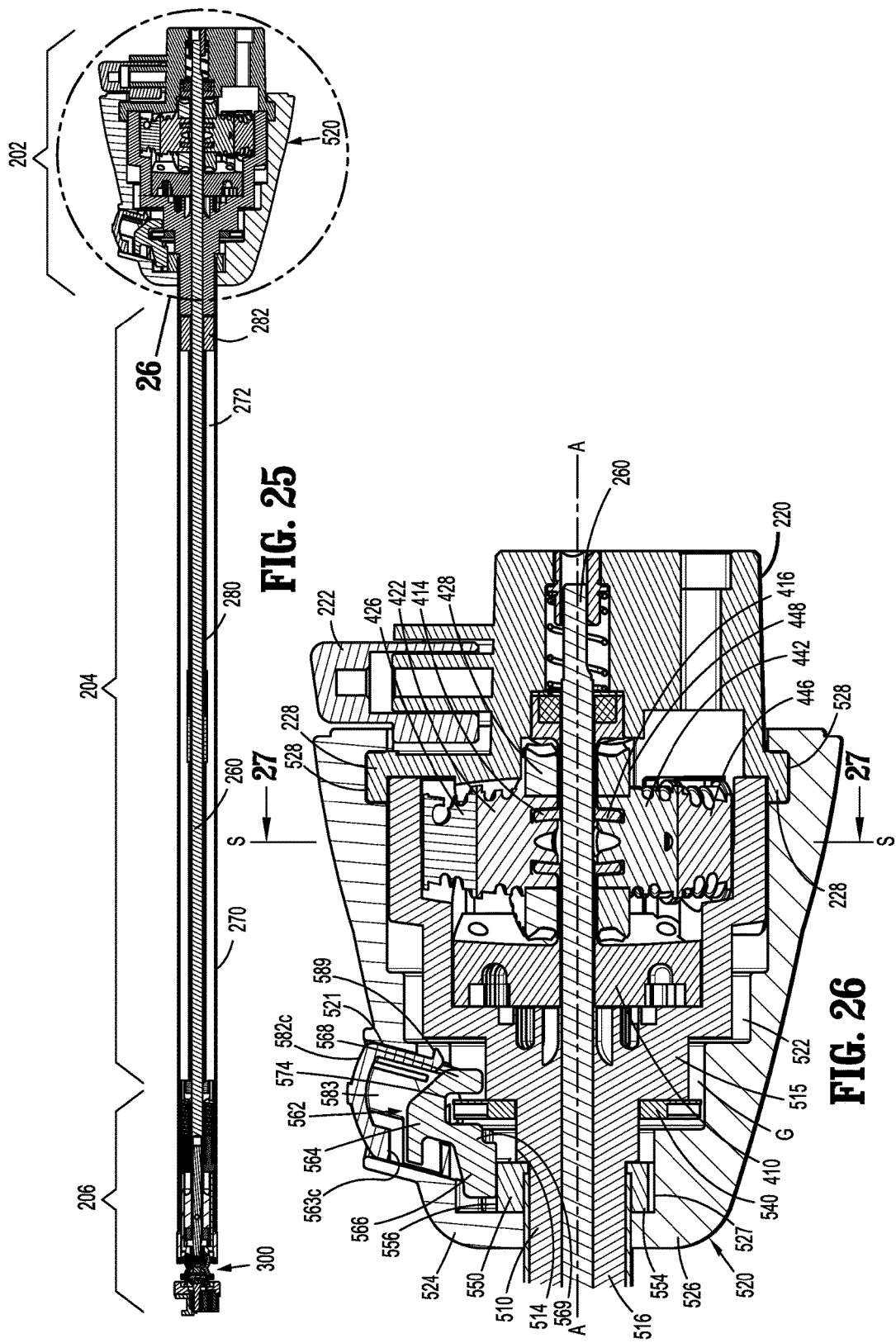

ADAPTER WITH CENTERING MECHANISM FOR ARTICULATION JOINT

BACKGROUND

1. Technical Field

The present disclosure relates to surgical instruments and, more specifically, to adapters including centering mechanisms for articulation joints of surgical instruments.

2. Discussion of Related Art

A number of surgical instrument manufacturers have developed product lines with proprietary powered drive systems for operating and/or manipulating surgical instruments. In many instances, the surgical instruments include a powered handle assembly, which is reusable, and a disposable end effector or the like that is selectively connected to the powered handle assembly prior to use and then disconnected from the powered handle following use in order to be disposed of or in some instances resterilized for re-use.

Generally, adapters of existing surgical instrument translate and deliver power from the handle assemblies, electromechanically or manually, to the end effectors. The adapters may support an articulation joint or joints for articulating the end effectors relative to a longitudinal axis of the adapter. To improve accessibility to a surgical site, the articulation joints may be configured to articulate the end effector about a variety of axes in relation to the longitudinal axis of the adapter and may include multiple joints or a universal joint to achieve a desired articulation angle for the end effector.

When an articulation joint includes multiple axes of articulation, the degree of articulation can be difficult to accurately control because when a force is applied to articulate the end effector, the end effector is articulated about multiple axes simultaneously. In addition, during actuation of the surgical instrument, the position of the joints relative to one another can vary in response to forces which are exerted between the handle and the end effector, and which pass through the joints. There is a continuing need to increase the accuracy of an articulation mechanism of an adapter supporting an end effector for articulation about a plurality of axes to maintain the position of the joints during actuation of the surgical instrument.

SUMMARY

In an aspect of the present disclosure, a joint assembly includes a proximal joint housing, a first hinge, a first ring, a joint cover, a second ring, a second hinge, and a biasing mechanism. The proximal joint housing defines a first longitudinal axis and includes the first hinge that is positioned at a distal portion of the proximal joint housing. The first ring is pivotally coupled to the first hinge about a first pivot axis that is orthogonal to and intersects the first longitudinal axis. The joint cover has first and second cover portions. The first cover portion is pivotally coupled to the first hinge about a second pivot axis that is orthogonal to and intersects the first pivot axis and the first longitudinal axis. The first and second pivot axes intersect the first longitudinal axis at a first joint center. The second ring is pivotally coupled to the second cover portion of the joint cover about a third pivot axis. The second hinge is pivotally coupled to the second ring about a fourth pivot axis that is orthogonal to the third pivot axis. The third and fourth pivot axes intersect at a second joint center that is spaced from the first joint center.

The cover axis of the joint cover is defined between the first and second joint centers. The biasing mechanism is engaged with the first ring and the joint cover to bias the joint cover towards an aligned configuration in which the cover axis is aligned with the first longitudinal axis.

In aspects, the biasing mechanism includes a pair of inner biasing bars and a pair of outer biasing bars. The pair of inner biasing bars may be engaged with the proximal portion of the joint cover and the pair of outer biasing bars may be engaged with the first ring. Each of the inner and outer basing bars of the pairs of inner and outer biasing bars may extend longitudinally and may be translatable in a direction parallel to the first longitudinal axis. Each of the inner and outer biasing bars of the pairs of inner and outer biasing bars may be operably associated with a respective biasing member that is configured to urge the associated biasing bar through the first hinge.

In some aspects, in the aligned configuration of the second hinge, a second longitudinal axis is aligned with the cover axis and the first longitudinal axis. The second longitudinal axis may pass through the second joint center and extend through the center of the second hinge. In a first articulated configuration of the joint assembly, the second longitudinal axis may be articulated relative to the cover axis with the joint cover in the aligned configuration. In a second articulated configuration of the joint assembly, the second longitudinal axis may be articulated relative to the cover axis and the cover axis may be articulated relative to the first longitudinal axis. The biasing mechanism may be configured to maintain the joint assembly in the first articulated configuration until the second longitudinal axis is articulated to a maximum angle of articulation relative to the cover axis. The maximum angle of articulation may be in a range of about 15° to about 45°.

In certain aspects, the joint assembly includes a first drive shaft, a joint body, and a second drive shaft. The first drive shaft may extend through the first hinge. The joint body may have first and second body portions. The first body portion may be rotatably disposed within the first cover portion and may be rotatably and pivotally coupled to the first drive shaft. The second body portion may be rotatably disposed within the second cover portion. The second drive shaft may extend through the second hinge. The second drive shaft may be rotatably and pivotally coupled to the second body portion. The first drive shaft may include a drive ball that is disposed within the first body portion. The first drive shaft may be rotatably disposed along the first longitudinal axis. The drive ball may define a center channel that is orthogonal to the first longitudinal axis and arced slots in a plane that is aligned with the first longitudinal axis and bisects the center channel.

In particular aspects, the joint assembly includes a center pin and a shaft pin. The center pin may be disposed within the center channel and may define a pin opening that is orthogonal to a central longitudinal axis of the center pin. The shaft pin may be disposed within the pin opening and the arced slots to rotatably couple the joint body to the first drive shaft. The arced slots and the shaft pin may cooperate to limit articulation between the first drive shaft and the joint body.

In aspects, the second drive shaft further includes a receiver. The receiver may be rotatably disposed within the second cover portion and may receive the second body portion. The joint cover may define a cover axis that passes through the first and second joint centers. The second body portion may define a center channel that is orthogonal to the cover axis and arced slots in a plane that is aligned with the cover axis and bisecting the center channel. The joint body may be rotatable along the cover axis.

In some aspects, the joint assembly includes a center pin and a shaft pin. The center pin may be disposed within the center channel and may define a pin opening that is orthogonal to a central longitudinal axis of the center pin. The shaft pin may be disposed within the pin opening and the arced slots to rotatably couple the joint body to the second drive shaft. The arced slots and the shaft pin may cooperate to limit articulation between the joint body and the second drive shaft.

In another aspect of the present disclosure, an adapter includes a proximal portion, an elongate portion, and a distal portion. The proximal portion is configured to couple to a handle. The elongate portion extends from the proximal portion and defines a first longitudinal axis. The distal portion is supported by the elongate portion and is configured to releasably couple to a tool assembly to the handle. The distal portion includes a joint assembly. The joint assembly includes a first hinge, a first ring, a joint cover, a second ring, a second hinge, and a biasing mechanism. The first hinge is disposed along the first longitudinal axis and is positioned at a distal end of the elongate portion. The first ring is pivotally coupled to the first hinge about the first pivot axis that is orthogonal to and intersects the first longitudinal axis. The joint cover has first and second cover portions. The first cover portion is pivotally coupled to the first hinge about a second pivot axis that is orthogonal to and intersects the first pivot axis and the first longitudinal axis. The first and second pivot axes intersect the first longitudinal axis at a first joint center. The second ring is pivotally coupled to the second cover portion of the joint cover about a third pivot axis. The second hinge is pivotally coupled to the second ring about a fourth pivot axis that is orthogonal to the third pivot axis. The third and fourth pivot axes intersect at a second joint center that is spaced form the first joint center. A cover axis of the joint cover is defined between the first and second joint centers. The biasing mechanism is engaged with the first ring and the joint cover to bias the joint cover towards an aligned configuration in which the cover axis is aligned with the first longitudinal axis.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 1 is a perspective view of an electromechanical system provided in accordance with the present disclosure;

FIG. 2 is a perspective view of an adapter and a tool assembly of the electromechanical system of FIG. 1 with the tool assembly in an unclamped position;

FIG. 11 is a cross-sectional view taken along section line 11-11 of FIG. 5;

FIG. 12 is an enlarged view of the indicated area of detail of FIG. 11;

FIG. 15 is a side view of the joint assembly of FIG. 5 in a aligned position;

FIG. 16 is a top view of a portion of the joint assembly of FIG. 15;

FIG. 17 is a cross-sectional view taken along section line 17-17 of FIG. 16;

FIG. 18 is a top view of the joint assembly of FIG. 16 with a distal joint of the joint assembly in an articulated position with the cables removed;

FIG. 20 is a side view of the joint assembly of FIG. 15 in another articulated position;

FIG. 21 is a side longitudinal cross-sectional view of the joint assembly of FIG. 20;

FIG. 25 is a cross-sectional view taken along section line 25-25 of FIG. 2;

FIG. 26 is an enlarged view of the indicated area of detail of FIG. 25;

DETAILED DESCRIPTION

Figure 3:
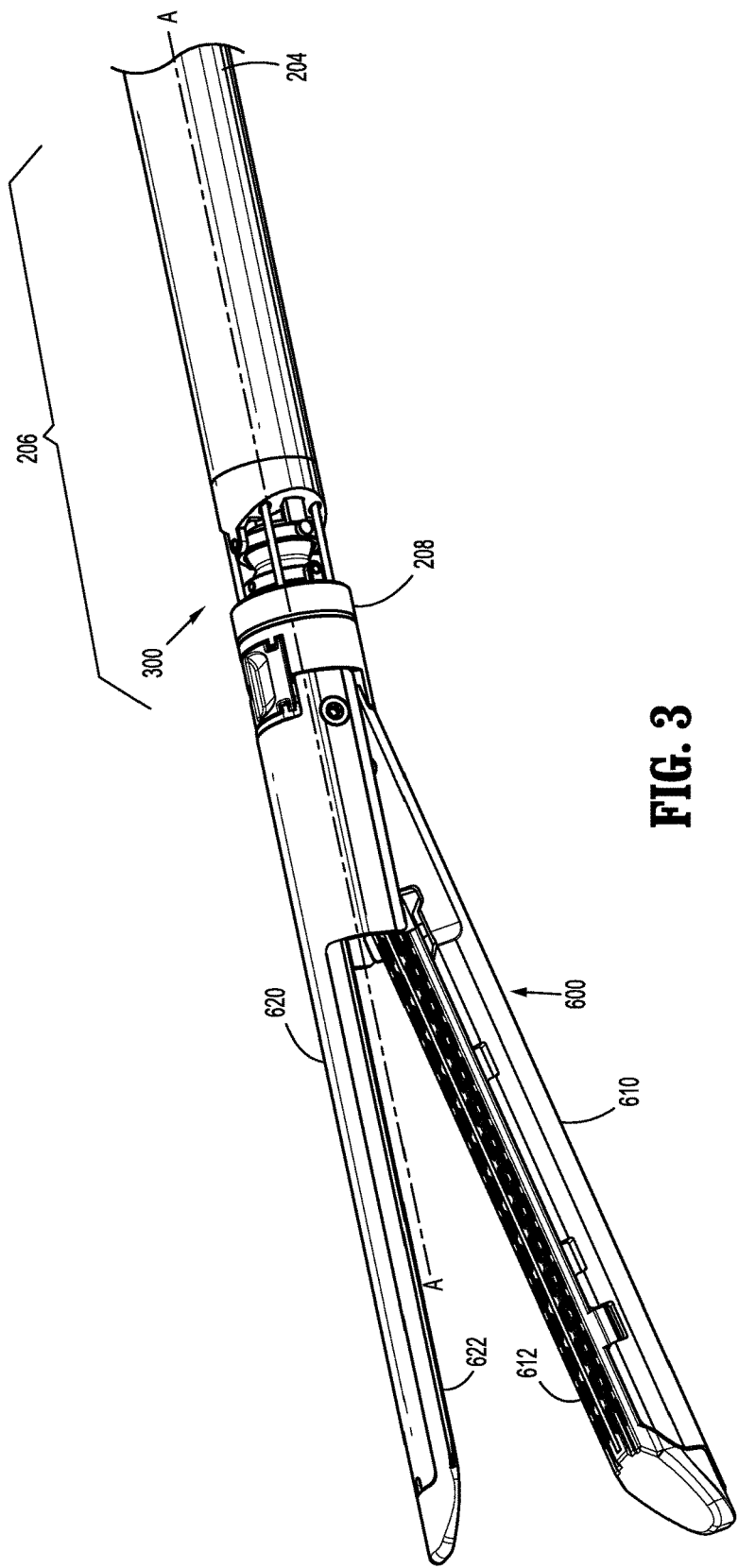
FIG. 3 is an enlarged view of the indicated area of detail of FIG. 2 with the tool assembly in an aligned position.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. In addition, the term "proximal" refers to the portion of the device or component thereof that is closest to the clinician and the term "distal" refers to the portion of the device or component thereof that is farthest from the clinician. Further, in the drawings and in the description that follows, terms such as "front", "rear", "upper", "lower", "top", "bottom" and the like are used simply for convenience of description and are not intended to limit the disclosure thereto.

This disclosure relates generally to an adapter for use with electromechanical surgical system. The adapter includes a joint assembly having proximal and distal joints. The proximal joint is biased to an aligned position and is adapted to remain in the aligned position until the distal joint reaches an articulation limit. When the distal joint reaches an articulation limit, the proximal joint articulates to permit additional articulation of the joint assembly. In addition, the proximal joint is adapted to return to the aligned position before the distal joint articulates away from the articulation limit.

The adapter also includes an articulation mechanism configured to articulate the joint assembly. The articulation mechanism includes four cables that extend from a proximal portion of the adapter to a distal portion of the adapter beyond the joint. The cables are adapted to be retracted and extended to manipulate or articulate the joint assembly. Cables on opposite sides of the joint assembly are associated with one another such that as one cable is retracted, the opposite cable is extended to control the position of the distal housing and thus, articulation of the joint assembly.

The adapter further includes a roll mechanism configured to selectively secure the distal portion of the adapter in a plurality of positions about a longitudinal axis of the adapter.

Referring now to FIG. 1, a surgical system 10 in accordance with the present disclosure includes a handle 100, an adapter 200, and a tool assembly 600 (e.g., an end effector, multiple- or single-use tool assembly). The handle 100 is configured for selective connection with the adapter 200, and, in turn, the adapter 200 is configured for selective connection with the tool assembly 600. Together, the handle 100 and the adapter 200 may cooperate to actuate the tool assembly 600. The surgical system 10 may be an electro-mechanically powered system and the handle 100 may be electrically powered, e.g., battery powered. In any of the embodiments disclosed herein, the adapter can be configured to be used with a robotic surgical system. In embodiments, the articulation joint assembly can be incorporated into a manually driven surgical device.

The handle 100 includes a drive mechanism (not shown) that is configured to drive shafts and/or gear components to perform various operations of the electromechanical surgical system 10. In particular, the drive mechanism is configured to rotate a proximal drive shaft 260 (FIG. 23), a first articulation shaft 430 (FIG. 23), and a second articulation shaft 450 (FIG. 23) to actuate the tool assembly 600 and to articulate the tool assembly 600 relative to a longitudinal axis A-A (FIG. 2) of the adapter 200 as described in detail below. For a detailed description of an exemplary powered handle, reference may be made to U.S. Patent Publication No. 2015/0272577 and U.S. Pat. No. 9,055,943. The entire contents of each of these disclosures are incorporated by reference herein.

Figure 4:
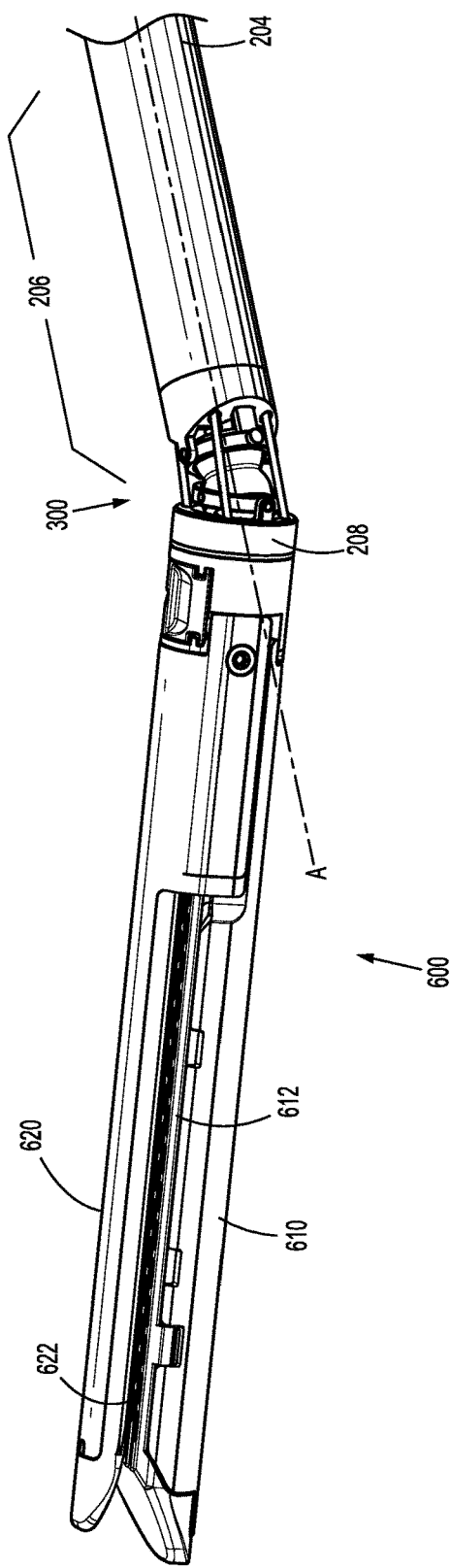
FIG. 4 is a perspective view of the tool assembly and a distal portion of the adapter of FIG. 2 in a first articulated position.

With reference also to FIGS. 2-5, the adapter 200 includes a proximal portion 202, an elongate portion 204, a distal portion 206, and a tool assembly connector 208. The proximal portion 202 is configured to couple the adapter 200 to the handle 100 (FIG. 1). The elongate portion 204 extends from the proximal portion 202 of the adapter 200 to the distal portion 206 of the adapter 200 and defines the longitudinal axis A-A of the adapter 200. The distal portion 206 includes a joint assembly 300 that is configured to articulate the tool assembly connector 208 relative to the longitudinal axis A-A as shown in FIG. 4 and described in detail below, causing the tool assembly 600 to articulate from a non-articulated position in which a longitudinal axis D-D (FIG. 18) of the tool assembly 600 is aligned with the longitudinal axis A-A of the adapter 200 to articulated position in which the longitudinal axis D-D of the tool assembly 600 is misaligned with the longitudinal axis A-A. The tool assembly connector 208 is positioned distal of the distal portion 206 and is configured to couple the tool assembly 600 to the adapter 200.

With particular reference to FIGS. 3 and 4, the tool assembly 600 includes a first jaw member 610 and a second jaw member 620 that are moveable relative to one another between an open configuration (FIG. 3) and a closed or clamped configuration (FIG. 4). As described in detail below, the joint assembly 300 allows for manipulation of the tool assembly 600 between a non-articulated position and a plurality of articulated positions. As shown, the tool assembly 600 is configured as a stapler with the first jaw member 610 releasably receiving a staple cartridge 612 having a plurality of staples (not shown) and the second jaw member including an anvil 622.

Figure 5:
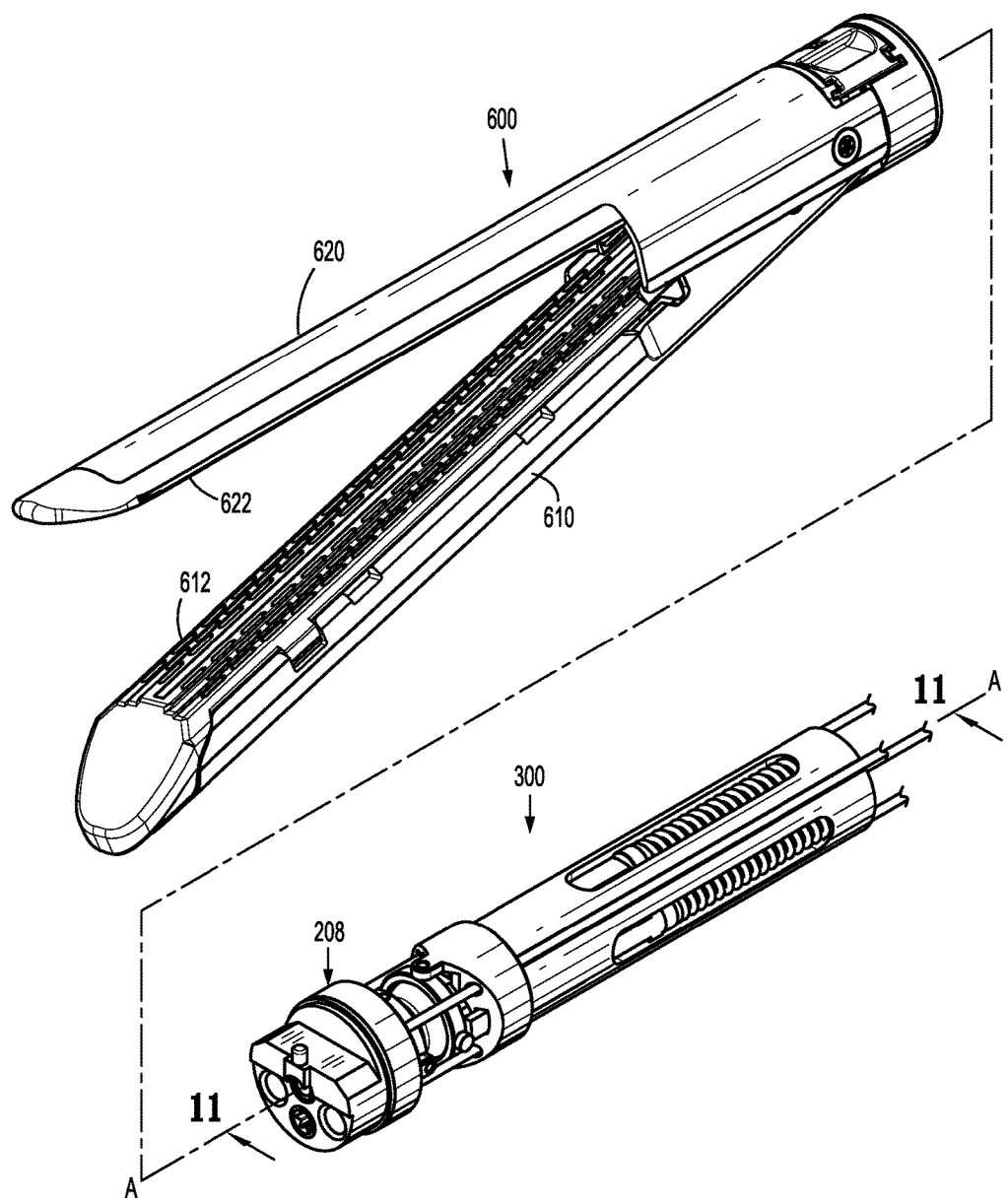
FIG. 5 is a perspective view of the tool assembly of FIG. 2 separated from a joint assembly of the adapter of FIG. 2.
Figure 6:
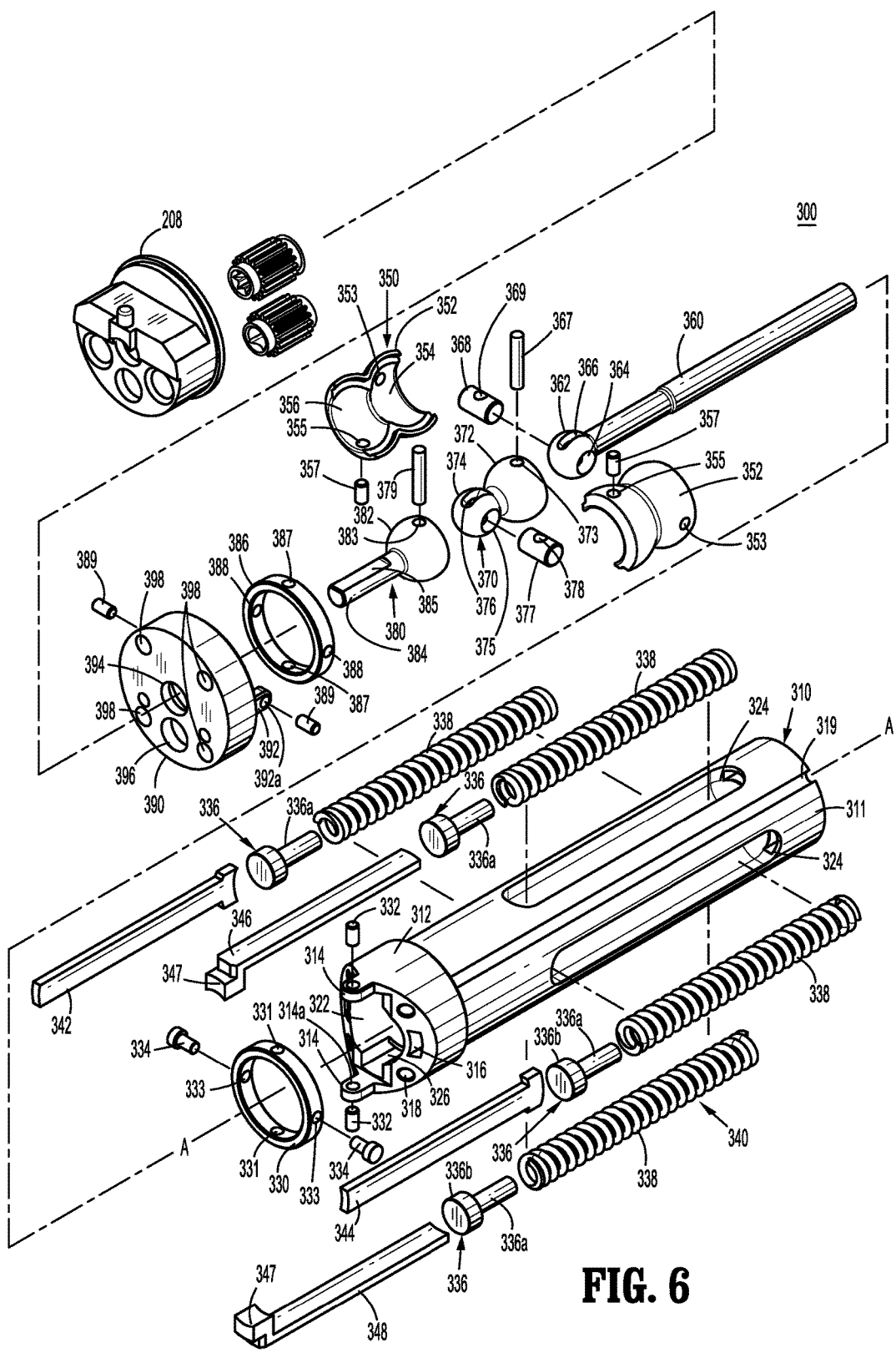
FIG. 6 is an exploded view, with parts separated, of the joint assembly of FIG. 5.

Referring to FIGS. 5 and 6, the joint assembly 300 is configured to control articulation of the tool assembly connector 208. The joint assembly 300 includes a proximal joint housing 310, a proximal ring 330, a biasing assembly 340, a joint cover 350, a central drive shaft 360, a joint body 370, a distal drive shaft 380, a distal ring 386, and a distal joint housing 390.

The proximal joint housing 310 extends along the longitudinal axis A-A of the adapter 200 such that the longitudinal axis A-A is coaxial with a longitudinal axis of the proximal joint housing 310. The central drive shaft 360 is rotatably disposed along the longitudinal axis A-A of the adapter 200 within the proximal joint housing 310. The joint body 370 receives a distal portion of the central drive shaft 360 such that the joint body 370 rotates in response to rotation of the central drive shaft 360. A portion of the joint body 370 is received within the distal drive shaft 380 such that the distal drive shaft 380 rotates in response to rotation of the joint body 370. The joint cover 350 is positioned over the joint body 370 such that the joint body 370 is rotatable within the joint cover 350. The proximal ring 330 is pivotally secured about a portion of the joint cover 350 and is engaged by the biasing assembly 340 to bias the joint body 370 towards an aligned position as detailed below. The distal ring 386 is pivotally secured about a portion of the joint cover 350 and is secured to the distal joint housing 390 to pivotally secure a portion of the joint cover 350 to the distal joint hinge 390.

With additional reference to FIG. 7-14, the proximal joint housing 310 is substantially cylindrical and defines a central lumen 322 therethrough. The proximal joint housing 310 includes a cylindrical portion 311 and a proximal or first hinge 312. The cylindrical portion 311 of the proximal joint housing 310 is sized and dimensioned to be received within the elongate portion 204 (FIG. 2) of the adapter 200 such that the central lumen 322 of the proximal joint housing 310 is coaxial with the longitudinal axis A-A of the adapter 200. The proximal hinge 312 is supported on a distal portion of the cylindrical portion 311 and is sized to extend distally from the elongate portion 204 of the adapter 200 (FIG. 4). An outer surface of the proximal hinge 312 may be dimensioned to form a contiguous surface with an outer surface of the elongate portion 204. The proximal hinge 312 may form a lip 313 (FIG. 7) about the cylindrical portion 311 that is positioned to engage an outer edge of the elongate portion 204 of the adapter 200 to axially fix the position of the proximal joint housing 310 relative to other components of the elongate portion 204 and prevent the proximal hinge 312 from passing into an outer tube of the elongate portion 204.

Figure 7:
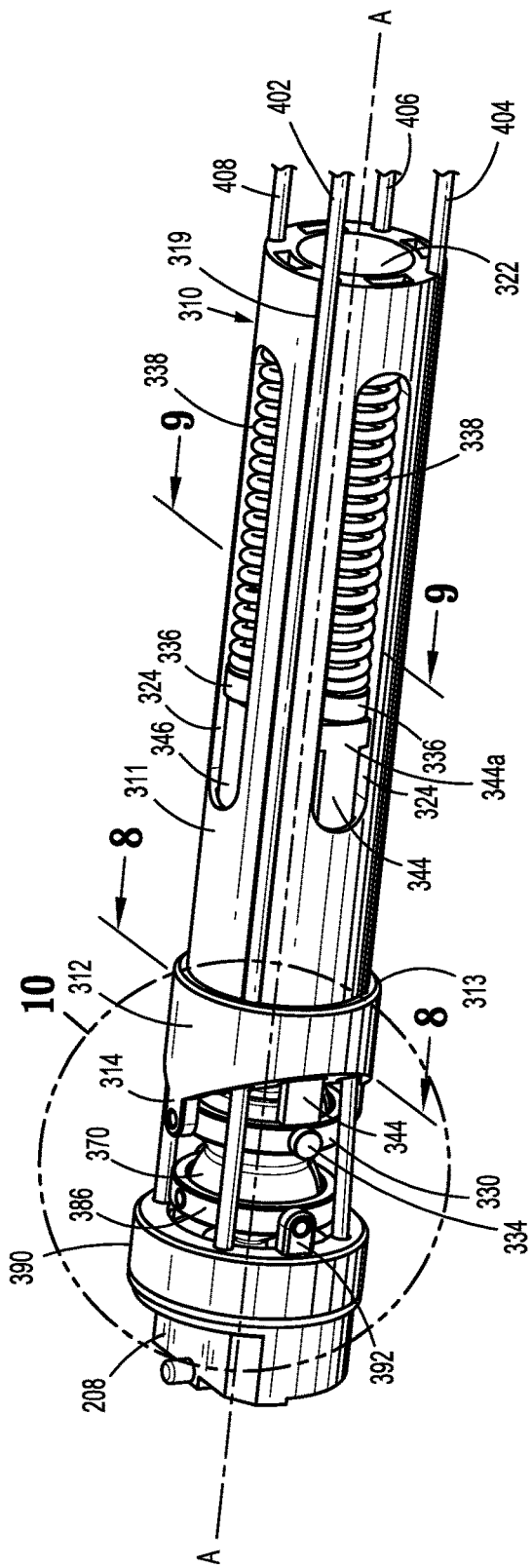
FIG. 7 is a rear perspective view of the joint assembly of FIG. 5.
Figure 8:
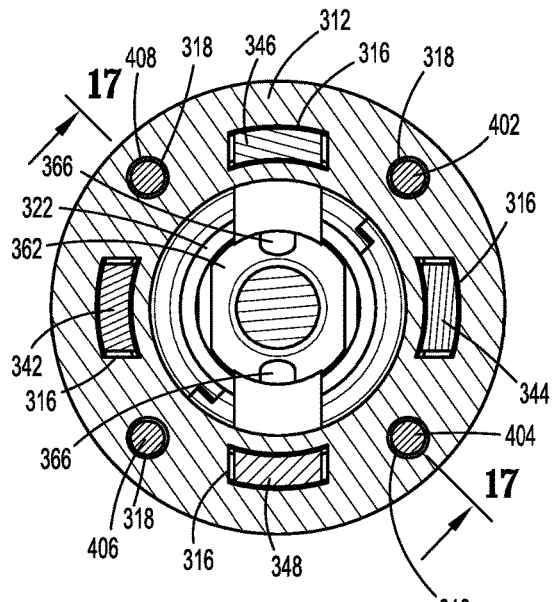
FIG. 8 is a cross-sectional view of taken along section line 8-8 of FIG. 7.
Figure 9:
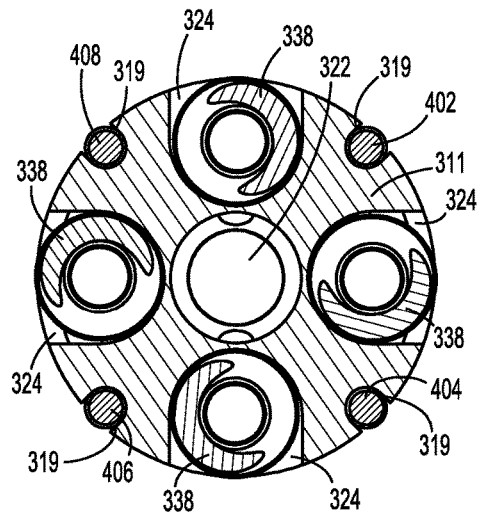
FIG. 9 is a cross-sectional view of taken along section line 9-9 of FIG. 7.

With particular reference to FIGS. 7-9, the biasing assembly 340 is disposed within the central lumen 322 of the proximal joint housing 310 and is engaged with the proximal ring 330 and joint body 370 to bias the joint body 370 towards a non-articulated or aligned position (FIG. 7). The biasing assembly 340 includes plungers 336, biasing members 338, outer bias bars 342, 344, and inner bias bars 346, 348. The proximal joint housing 310 defines windows 324 that are each sized and dimensioned to receive a respective biasing member 338 such that a proximal portion of the biasing member 338 is longitudinally fixed within the proximal joint housing 310. A distal portion of each of the biasing members 338 receives a shaft 336*a* of a respective one of the plungers 336 (FIG. 11) such that the plunger 336 is urged distally by the biasing member 338. The proximal joint housing 310 also defines bar passages 316 (FIG. 8) that are sized and dimensioned to receive a respective one of the bias bars 342-348. Each of the bias bars 342-348 is slidably disposed within one of the bar passages 316 and includes a proximal portion engaged with a respective one of the plungers 336. In embodiments, each plunger 336 includes a distal plate 336*b* and a shaft 336*a* extending proximally from the plate 336*b* such that the shaft 336*a* is received within a coil of the respective biasing member 338 with the distal plate 336*b* engaged with a distal portion of the biasing member 338 as shown in FIG. 11. It will be appreciated that the bias bars 342-348 slide within the bar passages 316 in a direction substantially parallel to the longitudinal axis A-A of the adapter 200.

In some embodiments, a proximal portion of the bias bars 342-348 includes a wing (e.g., wing 344*a* (FIG. 7)) to increase the surface area of a portion of the bias bar 342-348 positioned to engage a respective plunger 336. It is envisioned that the bar passages 316 and the respective bias bar 342-348 may be dimensioned and/or configured to reduce chatter or non-longitudinal movement of the bias bar 342-348 within the bar passage 316 as the respective bias bar 342-348 slides within the bar passage 316.

Figure 13:
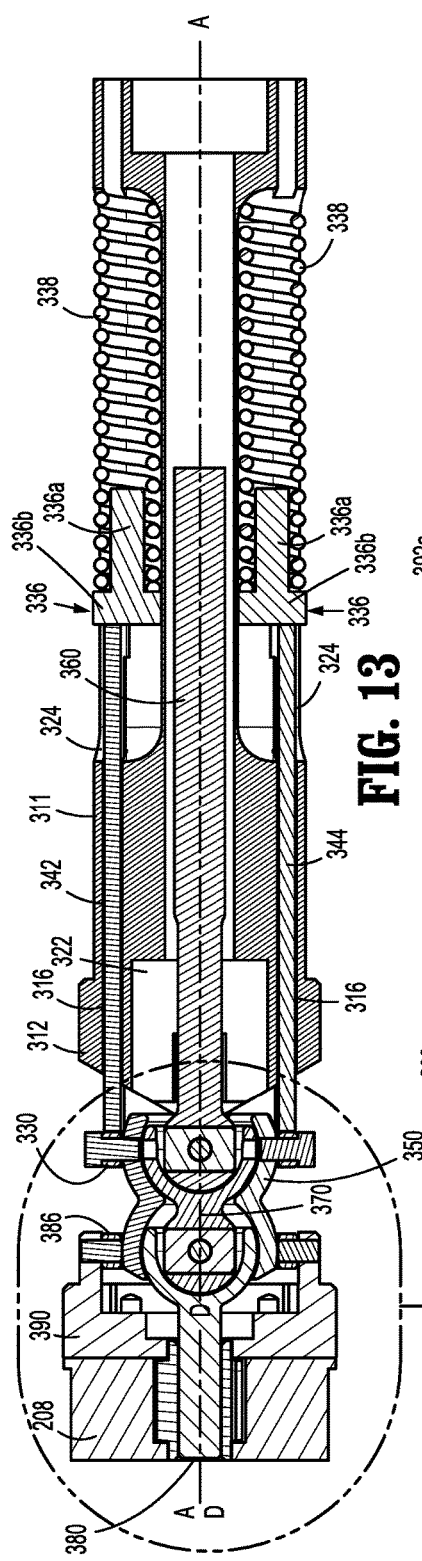
FIG. 13 is a cross-sectional view taken along section line 13-13 of FIG. 11.
Figure 14:
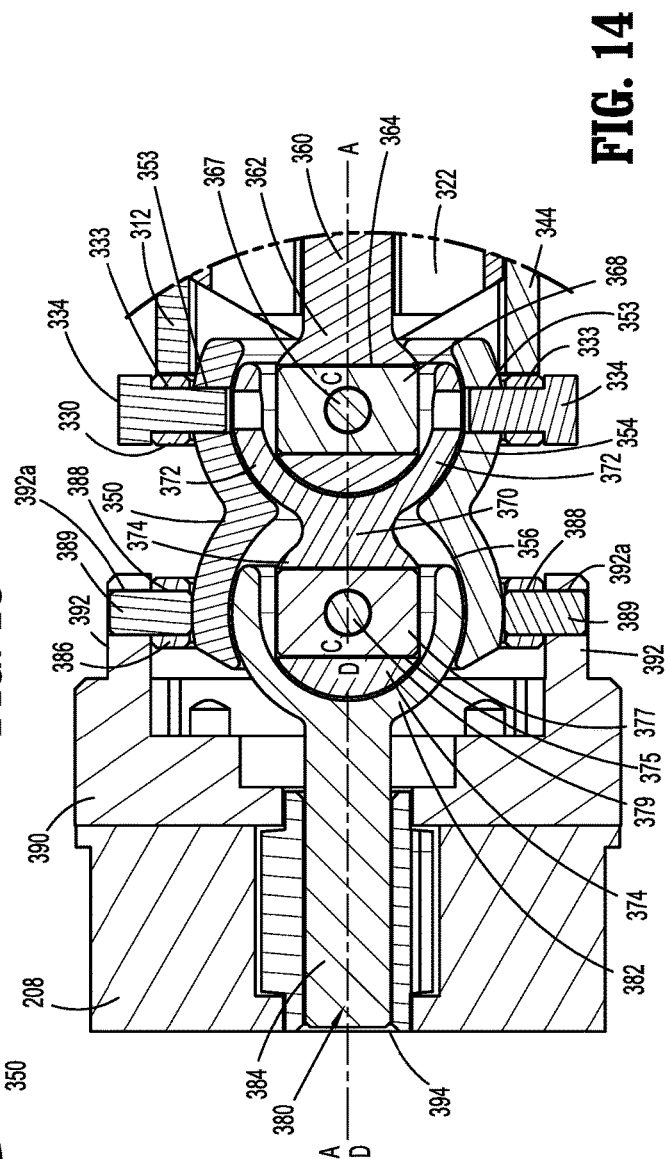
FIG. 14 is an enlarged view of the indicated area of detail of FIG. 13.

Referring to FIGS. 11-15, the outer bias bars 342, 344 are positioned on opposite sides of the proximal joint housing 310, with a distal portion of each of the outer bias bars 342, 344 engaged with the proximal ring 330 as shown in FIG. 14. The inner bias bars 346, 348 are positioned on opposite sides of the proximal joint housing 310, with a distal portion of each of the inner bias bars 346, 348 engaged with the joint cover 350 as shown in FIG. 12. The proximal joint housing 310 may define bar cutouts 326 in the proximal hinge 312 that slidably receive a stepped portion 347 (FIG. 12) of the inner bias bars 346, 348. The outer bias bars 342, 344 are radially offset approximately 90° from each of the inner bias bars 346, 348 such that each of the inner bias bars 346, 348 is radially positioned halfway between the outer bias bars 342, 344 and each of the outer bias bars 342, 344 is radially positioned halfway between the inner bias bars 346, 348 as shown in FIG. 8.

With reference to FIGS. 11-14, the proximal joint housing 310 is coupled to a proximal portion of the of the joint cover 350 such that the joint cover 350 is moveable in two degrees of freedom relative to the proximal joint housing 310. It will be appreciated that the joint cover 350 is rotatably fixed about the longitudinal axis A-A of the adapter 200 relative to the proximal joint housing 310.

Figure 10:
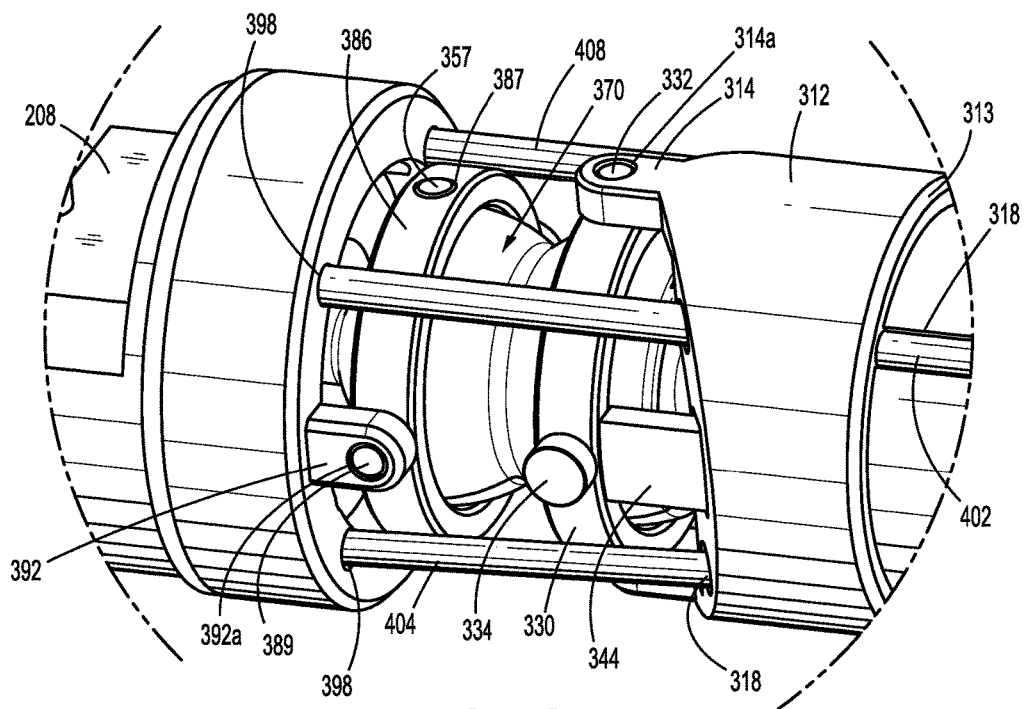
FIG. 10 is an enlarged view of the indicated area of detail of FIG. 7.

With particular reference to FIGS. 10-12, the proximal hinge 312 includes opposed flanges 314 (FIG. 10) on opposite sides of the central lumen 322 of the proximal joint housing 310. The proximal ring 330 is pivotally coupled to the flanges 314. Specifically, each of the flanges 314 defines a pin opening 314*a* and the proximal ring 310 defines pin openings 331 that are coaxially aligned with the pin openings 314*a* of the flange 314. A hinge pin 332 is received within each of the pin openings 331 and a pin opening 314*a* of a respective flange 314 to pivotally couple the proximal ring 330 to the flanges 314 of the proximal hinge 312. It will be appreciated that the proximal ring 330 pivots relative to the proximal hinge 312 about a pivot axis defined by the hinge pins 332.

Referring now to FIGS. 6, 13, and 14, the proximal ring 330 is pivotally coupled to the joint cover 350 by housing pins 334. The proximal ring 330 defines pin openings 333 on opposite sides of the proximal ring 330 with each of the pin openings 333 positioned approximately halfway between the pin openings 331 as shown in FIG. 6. The joint cover 350 defines pin openings 353 that are coaxially aligned with the pin openings 333. The housing pins 334 are received within the pin openings 333 and 353 to pivotally couple the joint cover 350 to the proximal ring 330 about a pivot axis defined by the housing pins 334. In embodiments, the pivot axis defined by the housing pins 334 is orthogonal to the pivot axis defined by the hinge pins 332 such that the joint cover 350 is moveable in two degrees of freedom relative to the proximal hinge 312. Alternatively, other pivot axis orientations are envisioned.

Referring again to FIGS. 11-14, a distal portion of the joint cover 350 is coupled the distal joint housing 390 by the distal ring 386 such that the distal joint housing 390 is moveable in two degrees of freedom relative to the joint cover 350. It will be appreciated that the distal joint housing 390 is rotatably fixed to the joint cover 350 and thus, the proximal hinge 312.

With particular reference to FIGS. 6, 11, and 12, a distal portion of the housing cover 350 is pivotally coupled to the distal ring 386 by housing pins 357 (FIG. 12). The distal ring 386 defines pin openings 387 on opposite sides of the distal ring 386. The joint cover 350 defines pin openings 355 that are coaxially aligned with the pin openings 387. The housing pins 357 are received within the pin openings 355 and 387 such that the joint cover 350 is pivotally coupled to the distal ring 386 about a pivot axis defined by the housing pins 357.

Referring to FIGS. 13 and 14, the distal joint housing 390 forms a distal hinge and defines a central opening 394 that is disposed along the longitudinal axis A-A of the joint assembly 300 in a non-articulated or aligned position as shown in FIG. 14. The distal joint housing 390 includes opposed flanges 392 (FIG. 6) on opposite sides of the central opening 394. The flanges 392 are radially offset approximately 90° from the flanges 314 of the proximal hinge 312 (FIG. 10) and are pivotally coupled to the distal ring 386. Specifically, each of the flanges 392 defines a pin opening 392*a* and the distal ring 386 defines pin openings 388 that are coaxially aligned with the pin openings 392*a* of the flanges 392. The pin openings 388 of the distal ring 386 are on opposite sides of the distal ring 386 with each of the pin openings 388 positioned approximately halfway between the pin openings 387 (FIG. 6). A hinge pin 389 is received within each of the pin openings 388 to pivotally couple the distal ring 386 to the distal joint housing 390 about a pivot axis defined by the hinge pins 389. It will be appreciated that the distal ring 386 pivots relative to the distal joint housing 390 about a pivot axis defined by the hinge pins 389. The pivot axis defined by the housing pins 357 is orthogonal to the pivot axis defined by the hinge pins 389 such that the joint cover 350 is moveable in two degrees of freedom relative to the distal joint housing 390.

Referring again to FIGS. 6 and 11-14, the central drive shaft 360, joint body 370, and distal drive shaft 380 pass through and are rotatable within the proximal joint housing 310, joint cover 350, and distal joint housing 390 such that the distal drive shaft 380 rotates in response to rotation of the central drive shaft 360 in a plurality of articulated positions of the joint assembly 300. The joint body 370 includes a proximal receiver 372 and a distal ball 374. The proximal receiver 372 is disposed within a proximal cavity 354 defined in a proximal portion of the joint cover 350. The central drive shaft 360 includes a drive ball 362 that is received within the proximal receiver 372 such that the centers of the drive ball 362, the proximal receiver 372, and the proximal cavity 354 are coincident with one another. The drive ball 362 defines a center channel 364 that passes through the center of the drive ball 362 transverse to the longitudinal axis A-A of the adapter 200 and receives a center pin 368 therethrough. The center pin 368 defines a pin opening 369 that is transverse to a longitudinal axis of the center pin 368. The drive ball 362 also defines arced slots 366 that are in communication with the center channel 364. The proximal receiver 372 of the joint body 370 defines pin openings 373. A proximal shaft pin 367 passes through the pin openings 373, the slots 366, and the pin opening 369 to rotatably fix the central drive shaft 360 to the joint body 370 such that the joint body 370 rotates in response to rotation of the central drive shaft 360. The arced slots 366 allow for one degree of freedom between the central drive shaft 360 and the joint body 370.

The distal drive shaft 380 includes a distal receiver 382 and a distal shaft 384 that extends distally from the distal receiver 382. The distal receiver 382 is disposed within a distal cavity 356 defined by the joint cover 350 and receives the distal ball 374 of the joint body 370 such that centers of the distal cavity 356, the distal receiver 382, and the distal ball 374 are coincident with one another. The distal ball 374 defines a center channel 375 that passes through the center of the distal ball 374 transverse to a longitudinal axis of the joint body 370 and receives a center pin 377 therethrough. The center pin 377 defines a pin opening 378 (FIG. 6) that is transverse to the longitudinal axis of the center pin 377. The distal ball 374 also defines arced slots 376 (FIG. 6) that are in communication with the center channel 375 and the distal receiver 382 defines pin openings 383. A distal shaft pin 379 passes through the pin openings 383, the slots 376, and the pin opening 378 to rotatably fix the joint body 370 with the distal receiver 382 such that the distal drive shaft 380 rotates in response to rotation of the joint body 370. The arced slots 376 allow for one degree of freedom between the joint body 370 and the distal drive shaft 380. The arced slots 366 (FIG. 12) of the drive ball 362 are defined in the same plane as the arced slots 376 of the distal ball 374; however, it is contemplated that a plane of the arced slots 366 may be radially offset from a plane of the arced slots 376 to allow for allow for multiple degrees of freedom between the distal drive shaft 380 and the central drive shaft 360.

Referring now to FIGS. 15-17, the adapter 200 (FIG. 2) includes an articulation mechanism 400 that manipulates the joint assembly 300. The articulation mechanism 400 and joint assembly 300 cooperate to control articulation of the joint assembly 300 before, during, and after actuation of the tool assembly 600 (FIG. 5). For example, when the tool assembly 600 is actuated to clamp tissue, fire staples through the clamped tissue, and/or sever tissue, the articulation mechanism 400 and joint assembly 300 cooperate to reduce chatter and maintain the position of the tool assembly 600 in relation to the adapter 200 during the each function of the tool assembly 600.

The articulation mechanism 400 includes cables 402, 404, 406, and 408 (FIG. 7) that extend through the elongate portion 204 (FIG. 2) of the adapter 200 from a proximal portion 202 (FIG. 2) of the adapter 200 to the distal portion 206 (FIG. 2) of the adapter 200. Each of the cables 402-408 is slidably disposed within one of four cable grooves 319 defined in an outside surface of the proximal joint housing 310 and passes through a respective one of four cable passages 318 (FIG. 8) in the proximal hinge 312. Each of the cables 402-408 passes from the proximal joint housing 310 to the distal joint housing 390. Each of the cables 402-408 includes a distal retainer (FIG. 17) (e.g., distal retainer 407 of cable 406 and distal retainer 409 of cable 408) that is received within a respective cable receiver 398 defined in the distal joint housing 390. Receipt of the distal retainers within the respective cable receivers 398 of the distal joint housing 390 facilitates application of tension to the distal joint housing 390.

The cables 402-408 are radially spaced about the longitudinal axis A-A to facilitate manipulation of the joint assembly 300 such that the distal drive shaft 380, which defines a distal drive axis D-D, and the joint cover 350, which defines a cover axis C-C, can be moved between a plurality of articulated positions relative to the longitudinal axis A-A. As shown, the cables 402-408 are evenly spaced radially, e.g., approximately 90°, about the outer surface of the joint housing 310 with each of the cables 402-408 passing approximately halfway between adjacent windows 324 (FIG. 15) defined in the cylindrical portion 311. It is contemplated that the cables 402-408 may be unevenly spaced about the cylindrical portion 311.

As described in greater detail below, the articulation mechanism 400 translates one cable in response to translation of a diametrically opposite cable to maintain tension in each cable 402-408 to continuously apply tension to the distal housing 390. For example, as the articulation mechanism 400 draws cable 402 proximally, the articulation mechanism 400 simultaneously releases cable 406 permitting cable 406 to be drawn distally an amount approximately equal to the amount cable 402 was drawn proximally. Likewise, as the articulation mechanism 400 draws cable 406 proximally, the articulation mechanism 400 simultaneously releases cable 402 permitting cable 406 to be drawn distally an amount approximately equal to the amount cable 406 was drawn proximally. It will be appreciated that cable 404 is associated with cable 408 in a similar manner that cable 402 is associated with cable 406 as detailed above. By keeping each cable substantially taut, articulation of the distal drive axis D-D of the distal drive shaft 380 relative to the longitudinal axis A-A and articulation of the cover axis C-C of the joint cover 350 relative to the longitudinal axis A-A of the adapter 200 can be precisely controlled and maintained.

With reference to FIGS. 15-21, articulation of the joint assembly 300 is described in accordance with the present disclosure. The joint assembly 300 has a first or proximal joint 302 and a second or distal joint 304. The proximal joint 302 articulates about a pivot axis passing through a center point that is coincident with centers of the drive ball 362 of the central drive shaft 360, the proximal receiver 372 of the joint body 370, the proximal portion of the joint cover 350, and the proximal ring 330. The distal joint 304 articulates about a pivot axis passing through a center point that is coincident with centers of the distal ball 374 of the joint body 370, the distal receiver 382 of the distal drive shaft 380, the distal portion of the joint cover 350, and the distal ring 386. The cover axis C-C passes between the center points of the proximal and distal joints 302, 304. Each of the proximal and distal joints 302, 304 is articulable in two degrees of freedom in response to actuation of the distal joint housing 390 by the articulation mechanism 400.

The joint assembly 300 has a centered or aligned position in which the distal drive axis D-D of the distal drive shaft 384 and the cover axis C-C of the joint cover 350 are coaxial with the longitudinal axis A-A of the proximal drive shaft 360 as shown in FIGS. 15-17. In the aligned position, the center points of the proximal and distal joints 302, 304 are both disposed along the longitudinal axis A-A. In addition, in the aligned position, planes defined by the proximal ring 330 and the distal ring 386 are parallel with one another and positioned orthogonal to the longitudinal axis A-A of the adapter 200.

Figure 19:
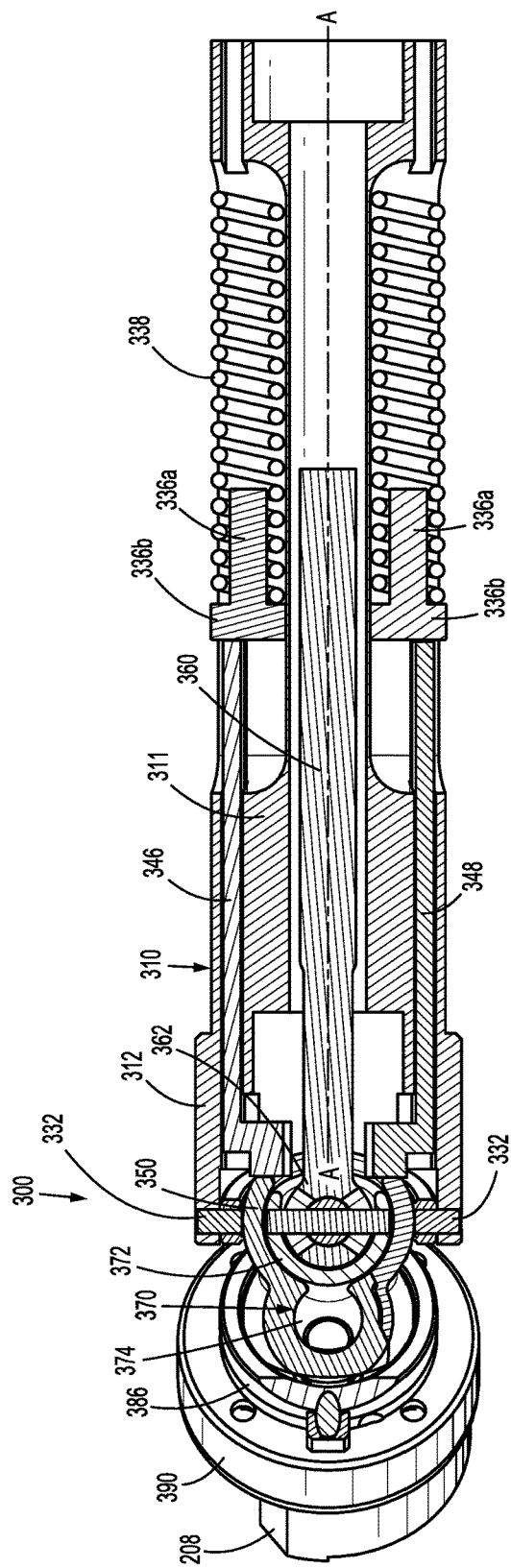
FIG. 19 is a cross-sectional view taken along section line 19-19 of FIG. 18.

Referring now to FIGS. 18 and 19, the joint assembly 300 has a first articulated position in which the distal joint 304 is articulated such that the distal drive axis D-D is articulated relative to the longitudinal axis A-A of the adapter 200 and the cover axis C-C of the joint cover 350 remains aligned with the longitudinal axis A-A. In addition, the center points of the proximal and distal joints 302, 304 remain disposed along the longitudinal axis A-A in the first articulated position. The biasing assembly 340 maintains the joint cover 350, and thus the cover axis C-C, in alignment with the longitudinal axis A-A until the distal joint 304 reaches an articulation limit, i.e., the position in which the distal shaft pin 379 reaches an end of the arced slots 376 (FIG. 12) of the distal ball 374 to prevent further independent articulation of the distal joint 304, i.e., independent of the proximal joint 302.

As shown in FIGS. 18 and 19, the articulation mechanism 400 is actuated to articulate the distal joint housing 390 to reposition the distal drive shaft 380 such that distal drive axis D-D defines an angle relative to the longitudinal axis A-A of the adapter 200 within an articulation limit of the distal joint 304. As shown, the distal housing 390 is articulated in the direction indicated by arrow "$X_1$" such that the distal drive axis D-D is repositioned in relation to the longitudinal axis A-A. During articulation of the joint assembly 300, the distal joint 304 is articulated and the biasing assembly 340 engages the proximal ring 330 and the joint cover 350 to maintain the cover axis C-C in alignment with the longitudinal axis A-A. The biasing assembly 340 prevents articulation of the joint cover 350 until the distal joint 304 reaches its articulation limit. Specifically, the outer bias bars 342, 344 are urged into engagement with the proximal ring 330 to maintain the joint cover 350 in alignment with the longitudinal axis A-A about a first axis, rotation about the pivot axis defined by the hinge pins 332, and the inner bias bars 346, 348 are urged into engagement with the joint cover 350 to maintain the joint cover 350 in alignment with the longitudinal axis A-A about another axis, rotation about the pivot axis defined by the housing pins 334. By maintaining the cover axis C-C of the joint cover 350 in alignment with the longitudinal axis A-A, the biasing assembly 340 maintains the proximal joint 302 in the aligned position. As shown, distal portions of the bias bars 342-348 engage the proximal ring 330 and the joint cover 350 with substantially planar surfaces such that a large force is required to initiate rotation of the proximal ring 330 and/or the joint cover 350 to articulate the cover axis C-C from the aligned position. This large force is only reached after the distal joint 304 is prevented from further articulation by distal shaft pin 379 reaching an end of the arced slots 376. It is contemplated that distal portions of the bias bars 342-348 may be arcuate to allow the cover axis C-C to articulate away from the aligned position with reduced force.

FIGS. 20 and 21 illustrate actuation of the articulation mechanism 400 to articulate the distal joint housing 390 to a second articulated position in which the distal drive axis D-D is repositioned relative to the longitudinal axis A-A of the adapter 200 to an angle beyond the articulation limit of the distal joint 304. As shown, the distal housing 390 is articulated in the direction indicated by arrow "$X_2$" such that the distal drive axis D-D and the cover axis C-C are repositioned relative to the longitudinal axis A-A from the position shown in FIG. 15. More specifically, when the distal joint 304 is articulated to its articulation limit, continued articulation of the distal joint housing 390 overcomes the biasing force applied by the biasing assembly 340 onto the proximal joint 302 such that the inner bias bar 346 compresses its associated biasing member 338 and the cover axis C-C of the joint cover 350 articulates relative to the longitudinal axis A-A about the proximal joint 302 in the direction indicated by arrow "$X_2$". As the proximal joint 302 articulates, the other inner bias bar 348 is urged distally by its associated biasing member 338 to translate distally and maintain engagement with the joint cover 350. In addition, the outer bias bars 342, 344 are urged distally by associated biasing members 338 to maintain engagement with the proximal ring 330. By independently maintaining each of the bias bars 342-348 in engagement with the joint cover 350 and/or the proximal ring 330, the position of the distal joint housing 390 is rigidly maintained for a given actuation of the articulation mechanism 400.

It will be appreciated that the biasing members 338 have a substantially linear spring constant and the bias bars 342-348 cooperate to urge the joint cover 350 and thus, the cover axis C-C, into alignment with the longitudinal axis A-A. As such, when the articulation mechanism 400 is actuated to return the distal joint housing 390 to the aligned position such that the distal drive axis D-D and the cover axis C-C are moved towards alignment with the longitudinal axis A-A, the biasing assembly 340 returns the cover axis C-C of the joint cover 350 and thus, the proximal joint 302 to the aligned position before the distal drive axis D-D is articulated from its articulation limit towards its aligned position.

In embodiments, the maximum angle of articulation of the proximal and distal joints 302, 304 may be equal to one another (e.g., 30°) or different from one another (e.g., the maximum angle of articulation of the proximal joint 302 may be greater than or less than the maximum angle of articulation of the distal joint 304). It will be appreciated that the maximum angle of articulation of the articulation assembly 300 is the sum of the maximum angle of articulation of proximal joint 302 and the maximum angle of articulation of the distal joint 304.

By controlling the order of articulation of the proximal and distal joints 302, 304 (i.e., ensuring that the distal joint 304 articulates to its articulation limit before the proximal joint 302 is articulated and returning the proximal joint 302 to its aligned position before articulating the distal joint 304 towards its aligned position), articulation of the joint assembly 300 is more predictable such that the location of the tool assembly 600 (FIG. 2) during articulation is more predictable. In addition, the biasing of the joint cover 350 into alignment with the longitudinal axis may provide a more stable and rigid joint assembly 300 by automatically adjusting for cable stretch to reduce cable backlash in the joint assembly 300. Further, by providing constant tension on the distal joint housing 390 from each of the cables 402-408, chatter experienced during actuation of the tool assembly 600 can be minimized.

Referring now to FIGS. 22-27, the proximal portion 202 of the adapter 200 includes a connector 220, the articulation mechanism 400, and a roll mechanism 500. The connector 220 is secured to the proximal portion 202 of the adapter 200 and releasably couples the adapter 200 to the handle 100 (FIG. 1). The handle 100 is configured to selectively rotate a proximal drive shaft 260 and to manipulate the articulation mechanism 400 when the connector 220 is releasably coupled to the handle 100. The proximal drive shaft 260 extends along the longitudinal axis A-A of the adapter 200 and extends through the elongate portion 204 to effect rotation of the central drive shaft 360 (FIG. 6). The elongate portion 204 also includes a central tube 280 that is coaxially disposed about the proximal drive shaft 260 and an outer tube 270 coaxially disposed about the central tube 280 to define a channel 272 therebetween.

Figure 23:
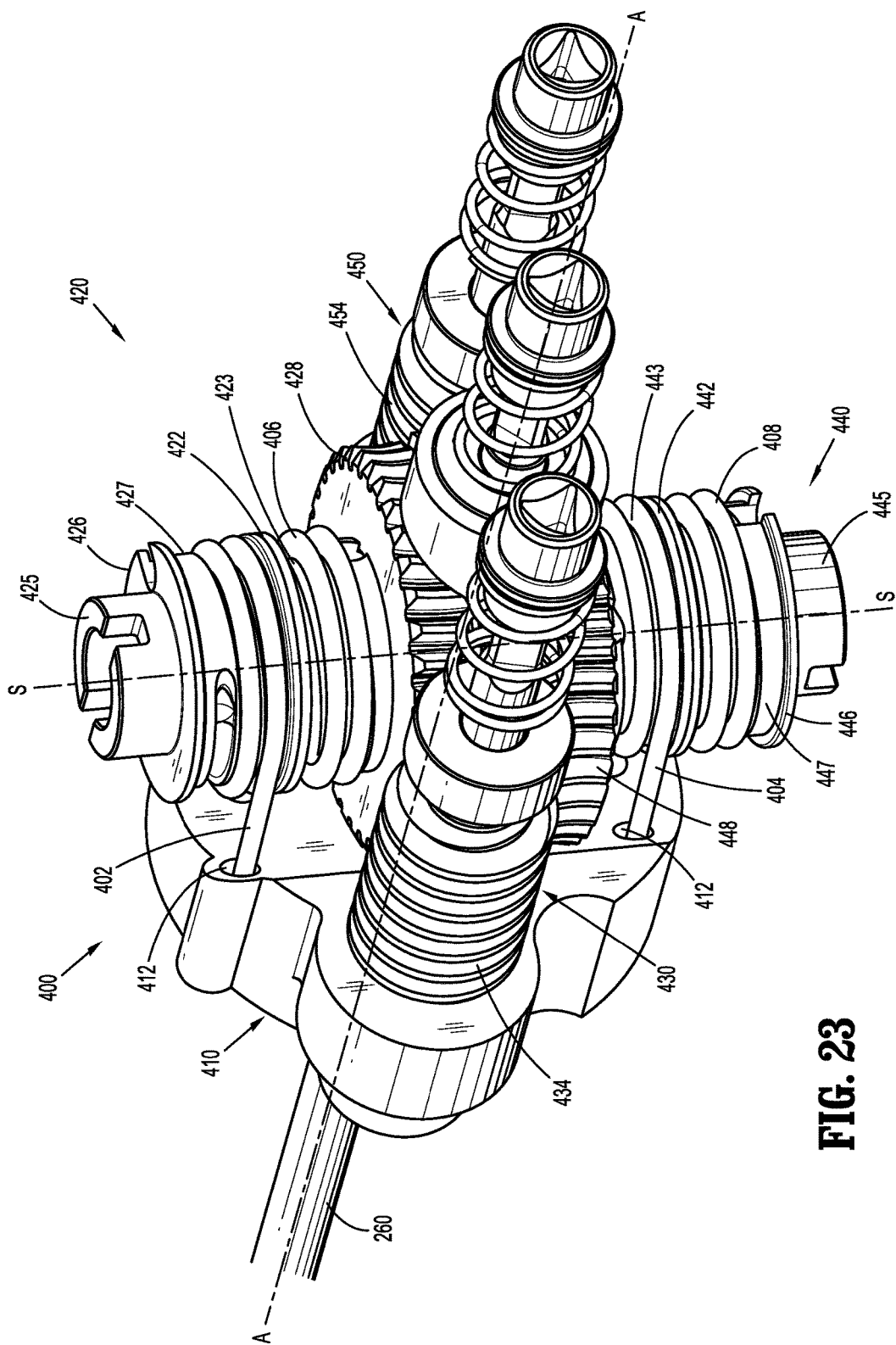
FIG. 23 is a rear perspective view of an articulation assembly of the proximal portion of the adapter.

The articulation mechanism 400 manipulates the cables 402-408 to articulate the joint 300 relative to the longitudinal axis A-A. With particular reference to FIG. 23, the articulation mechanism 400 includes an articulation body 410, a first or upper spindle assembly 420, a first articulation shaft 430, a second or lower spindle assembly 440, and a second articulation shaft 450. The upper spindle assembly 420 and the lower spindle assembly 440 are rotatably supported on the articulation body 410 about a spindle axis S-S that is transverse to the longitudinal axis A-A. The upper spindle assembly 420 is disposed on the upper side of the articulation body 410 and the lower spindle assembly 440 is disposed on the lower side of the articulation body 410.

Figure 24:
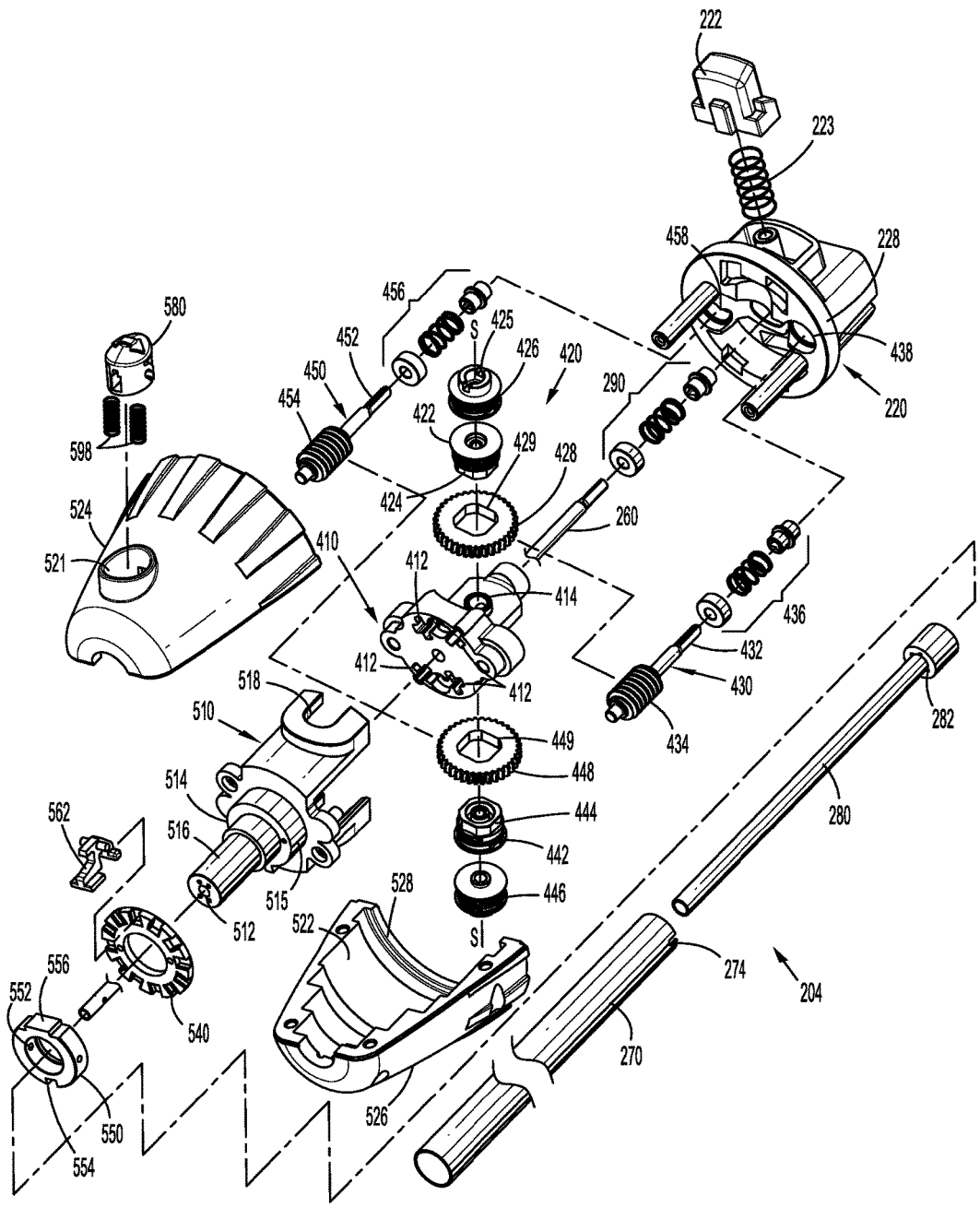
FIG. 24 is an exploded view, with parts separated, of the proximal portion of the adapter of FIG. 2.

With particular reference to FIG. 24, the upper spindle assembly 420 includes an inner spindle 422, an outer spindle 426, and a gear 428. The inner spindle 422 is substantially cylindrical and defines a helical groove 423 (FIG. 23) along an outer surface of the inner spindle 422. The inner spindle 422 includes a keyed protrusion 424 that extends towards the articulation body 410 and is disposed about an upper race 414 of the articulation body 410. The upper gear 428 defines a keyed opening 429 that receives the keyed protrusion 424 such that the inner spindle 422 rotates in response to rotation of the upper gear 428. The outer spindle 426 is substantially cylindrical and defines a helical groove 427 (FIG. 23) about an outer surface of the outer spindle 426. The outer spindle 426 includes an upper protrusion 425 that is rotatably received within a spindle recess 518 of the roll body 510. The roll body 510 retains the upper spindle assembly 420 over the upper race 414. The outer spindle 426 is rotatably fixed relative to the inner spindle 422 such that the outer spindle 426 rotates in response to rotation of the inner spindle 422. It is contemplated that the inner and outer spindles 422, 426 may be monolithically formed with one another. The helical grooves 423, 427 of the inner and outer spindles 422, 426, respectively, may form a single continuous helical groove.

The lower spindle assembly 440 includes an inner spindle 442, an outer spindle 446, and a gear 448. The inner spindle 442 is substantially cylindrical and defines a helical groove 443 (FIG. 23) about an outer surface of the inner spindle 442. The inner spindle 442 includes a keyed protrusion 444 that extends towards the articulation body 410 and is disposed about a lower race 416 of the articulation body 410. The lower gear 448 defines a keyed opening 449 that receives the keyed protrusion 444 such that the inner spindle 442 rotates in response to rotation of the lower gear 448. The outer spindle 446 is substantially cylindrical and defines a helical groove 447 (FIG. 23) about an outer surface of the outer spindle 446. In embodiments, the outer spindle 446 includes a lower protrusion 445 that is rotatably received within a spindle recess 518 of the roll body 510. The roll body 510 retains the lower spindle assembly 440 over the lower race 416. The outer spindle 446 is rotatably fixed relative to the inner spindle 442 such that the outer spindle 446 rotates in response to rotation of the inner spindle 442. It is contemplated that the inner and outer spindles 442, 446 may be monolithically formed with one another. The helical grooves 443, 447 of the inner and outer spindles 442, 446, respectively, may form a single continuous helical groove.

Referring back to FIGS. 22 and 23, the cables 402-408 extend from the proximal joint housing 310 (FIG. 6) of the joint assembly 300 to the proximal portion 202 of the adapter 200 through the channel 272 (FIG. 22) of the outer tube 270. As the cables 402-408 pass through the channel 272, the cables 402-408 are guided through holes 282 defined in a proximal cylinder 282 of the central tube 280. The cables 402 and 406 are guided through holes 284 on a first or upper side of the proximal cylinder 282 and the cables 404 and 408 are guided through holes 284 on a second or lower side of the proximal cylinder 282. The cables 402-408 pass through the holes 284 of the proximal cylinder 282 and into holes 512 of a roll body 510. The cables 402-408 pass through the holes 512 of the roll body 510 and into holes 412 defined in the articulation body 410 such that the cables 402, 406 are disposed on an upper side of the articulation body 410 and the cables 404, 408 are disposed on a lower side of the articulation body 40.

With particular reference again to FIG. 23, the cables 402, 406 pass from the holes 412 defined in the articulation body 410 and into the grooves 423, 427 of the upper spindle assembly 420 in opposite directions from one another. As shown, the cable 402 exits a hole 412 on a first side of the upper spindle assembly 420 and enters the groove 427 of the outer spindle 426. The cable 406 exits a hole 412 on a second side of the upper spindle assembly 420 and enters a groove 423 of the inner spindle 422. As the upper spindle assembly 420 rotates in a first direction (e.g., counter-clockwise when viewed from above in FIG. 23) the cable 402 is wound about the outer spindle 426 to retract or draw the cable 402 and the cable 406 is, simultaneously, unwound from about the inner spindle 422 to extend or release cable 406. As the upper spindle assembly 420 rotates in a second direction opposite the first direction (e.g., clockwise when viewed from above in FIG. 23) the cable 402 is unwound from about the outer spindle 426 to extend the cable 402 and the cable 406 is, simultaneously, wound about the inner spindle 422 to retract the cable 406. It will be appreciated that this corresponding retraction and extension applies tension to the distal joint housing 390 (FIG. 17) to articulate the joint 300 as detailed above.

The cables 404, 408 pass from the holes 412 defined in the articulation body 410 and into the grooves 443, 447 of the lower spindle assembly 440 in opposite directions from one another. As shown, the cable 404 exits a hole 412 on a first side of the lower spindle assembly 440 and enters the groove 443 of the inner spindle 442. The cable 408 exits a hole 412 on a second side of the lower spindle assembly 440 and enters a groove 447 of the outer spindle 446. As the lower spindle assembly 440 rotates in a first direction (e.g., counter-clockwise when viewed from above in FIG. 23) the cable 404 is wound about the inner spindle 442 to retract the cable 404 and the cable 408 is, simultaneously, unwound from about the outer spindle 446 to extend cable 408. As the lower spindle assembly 440 rotates in a second direction opposite the first direction (e.g., clockwise when viewed from above in FIG. 23) the cable 404 is unwound from about the inner spindle 442 to extend the cable 402 and the cable 406 is, simultaneously, wound about the outer spindle 446 to retract the cable 408. It will be appreciated that this corresponding retraction and extension applies tension to the distal joint housing 390 (FIG. 17) to articulate the joint 300 as detailed above.

Figure 27:
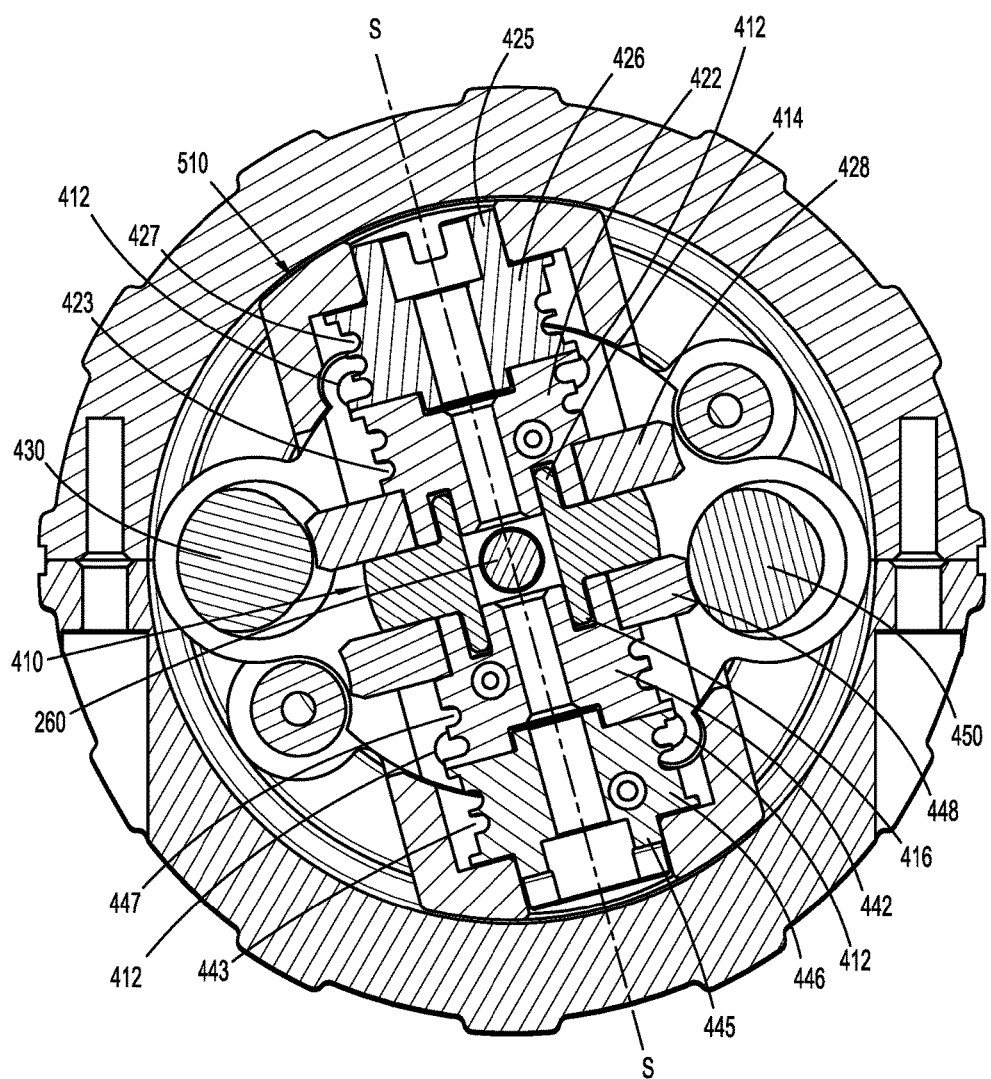
FIG. 27 is a cross-sectional view taken along section line 27-27 of FIG. 26.

With reference to FIGS. 24 and 27, the first articulation shaft 430 includes a gear 434 that is meshingly engaged with the gear 428 of the upper spindle assembly 420 to rotate the upper spindle assembly 420 about the spindle axis S-S in response to input from the handle 100 (FIG. 1). The handle 100 rotates the first articulation shaft 430 about a shaft axis that is parallel to and offset from the longitudinal axis A-A. The first articulation shaft 430 includes an input portion 432 that extends through an input hole 438 defined in the connector 220 and may include a bearing assembly 436 disposed about a proximal portion of the first articulation shaft 430 to rotatably mount the input portion 432 within the input hole 438 and/or to longitudinally bias the first articulation shaft 430.

The second articulation shaft 450 includes a gear 454 that is meshingly engaged with the gear 448 of the lower spindle assembly 440 to rotate the lower spindle assembly 440 about the spindle axis S-S in response to input from the handle 100 (FIG. 1). The handle 100 rotates the second articulation shaft 450 about a shaft axis that is parallel to and offset from the longitudinal axis A-A. The second articulation shaft 450 includes an input portion 452 that extends through an input hole 458 defined in the connector 220 and may include a bearing assembly 456 disposed about a proximal portion of the second articulation shaft 450 to rotatably mount the input portion 452 within the input hole 458 and/or to longitudinally bias the second articulation shaft 450.

With reference to FIGS. 22, 24, 26, and 28, the roll mechanism 500 is configured to rotate or roll the elongate portion 204 and the distal portion 206 of the adapter 100 (FIG. 2) about the longitudinal axis A-A. An example of a similar roll mechanism is described in U.S. patent application Ser. No. 15/229,220, filed Aug. 5, 2016, the entire contents of which are hereby incorporated by reference.

The roll mechanism 500 includes the roll body 510, a roll housing 520, and a locking mechanism 560. The roll body 510 is rotatably fixed to the articulation body 410 and the connector 220. The roll housing 520 is rotatably disposed about the roll body 510 with the locking mechanism 560 disposed within the roll housing 520. As will be described in further detail below, the locking mechanism 560 has a locked position (FIG. 3) in which the roll housing 520 is rotationally secured relative to the connector 220 and an unlocked position (FIG. 13) in which the roll housing 520 is rotatable about the longitudinal axis A-A in relation to the connector 220. The tool assembly 600 is rotatably fixed to the distal portion 206 of the adapter 100 which is rotatably fixed to the roll housing 520 such that rotation of the roll housing 520 about the longitudinal axis A-A of the adapter 100 causes the tool assembly 600 (FIG. 1) to rotate about the longitudinal axis A-A. This enables a clinician to orient the tool assembly 600 relative to the handle 100 (FIG. 1) without changing the orientation of the handle 100.

The roll housing 520 may be formed from a first body shell 524 and a second body shell 526. Each of the first and second body shells 524, 526 form approximately half of the roll housing 520 and may be joined together by fasteners (not explicitly shown). Alternatively, the first and second body shells 524 and 526 may be secured together by welding or the like. The first and second body shells 524, 526 define a cavity 522 that receives the roll body 510 which is coupled the central tube 280. The central tube 280 is rotatably fixed to the roll body 510. The connector 220 includes an annular flange 228 and the first and second body shells 524, 526 define a proximal annular groove 528 that is configured to receive the annular flange 228. The annular flange 228 longitudinally secures the roll housing 520 relative to the connector 220 while allowing the roll housing 520 to rotate about the connector 220, the roll body 510 and the central tube 280.

Figure 22:
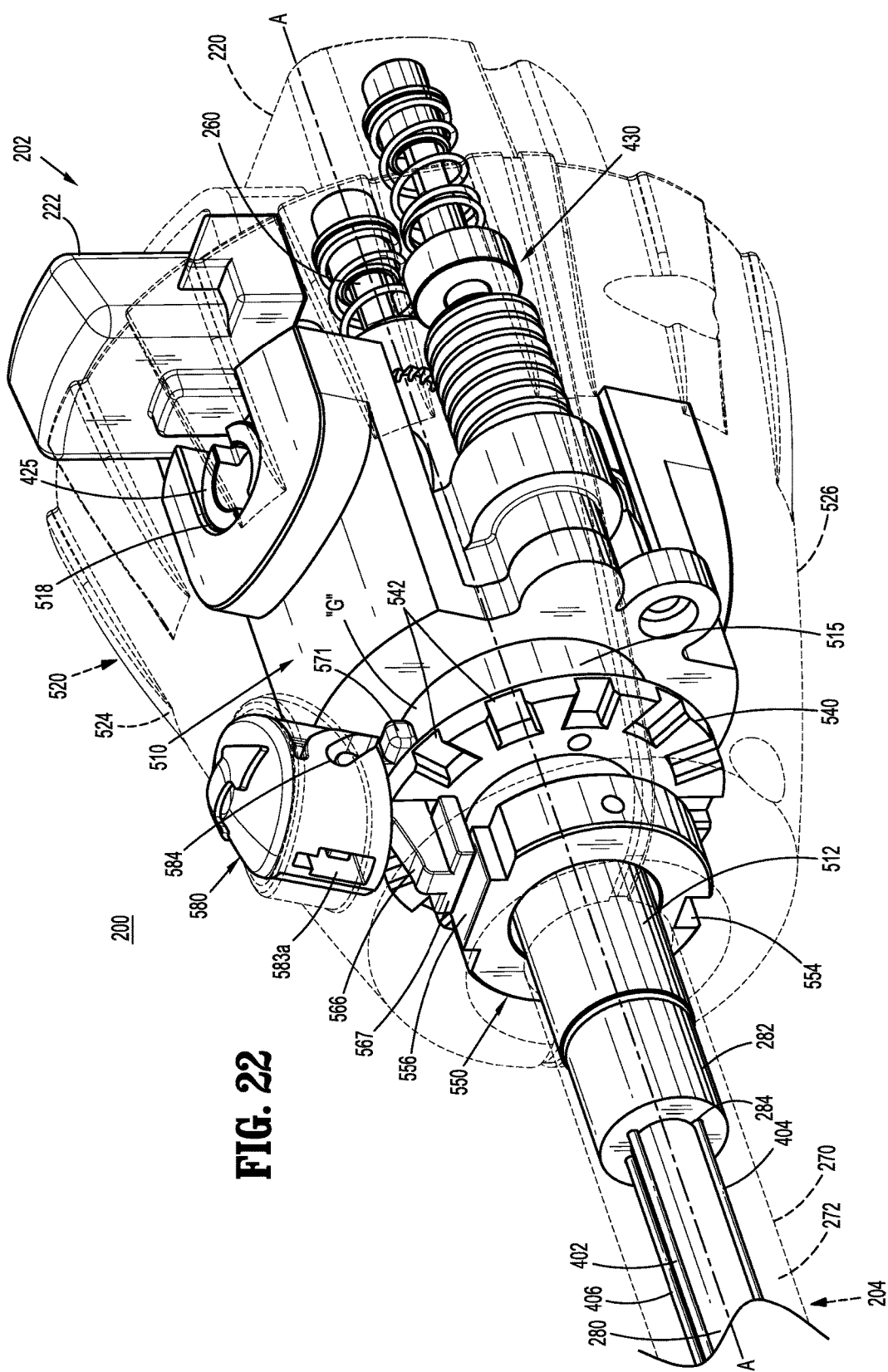
FIG. 22 is a perspective view of a proximal portion of the adapter of FIG. 2 with portions of the adapter shown in dashed lines.

With particular reference to FIGS. 22 and 24, the roll body 510 includes a locking race 514, a spacer 515, and a neck 516. Each of the locking race 514, the spacer 515, and the neck 516 are substantially cylindrical in shape and are coaxially disposed about the longitudinal axis A-A. In addition, each of the locking race 514, the spacer 515, and the neck 516 are positioned distal to the recess 518 defined by the roll body 510. The locking race 514 is positioned between the spacer 515 and the neck 516. The spacer 515 defines a gap "G" between the locking race 514 and a proximal portion of the roll body 510. The neck 516 distally extends from the locking race 514. The locking race 514 has a diameter greater than the neck 516 and less than the spacer 515. The holes 512 that receive the cables 402-408 extend through the neck 516, the locking race 514, and the spacer 515.

The roll mechanism 500 includes a locking disc 540 and a roll nut 550. The locking disc 540 is disposed about the locking race 514 and is rotationally fixed to the spacer 515 such that the gap "G" is defined between the locking disc 540 and the proximal portion of the roll body 510. The roll nut 550 is disposed about the neck 516 with a proximal portion 274 of the outer tube 270 disposed between the roll nut 550 and the neck 516. The roll nut 550 is rotatable relative to the neck 516 such that the roll nut 550 rotates about the longitudinal axis A-A. The proximal portion 274 of the outer tube 270 defines opposed notches 274 and the roll nut 550 includes opposed protrusion 552 that are disposed in the notches 274 such that the outer tube 270 rotates in response to rotation of the bearing 500 about the longitudinal axis A-A. The roll nut 550 also defines a keyway 554 that receives a key 527 of the second body shell 526 to rotatably fix the roll nut 550 to the roll housing 520 such that the roll nut 550 and the outer tube 270 rotate about the longitudinal axis A-A in response to rotation of the roll housing 520 as shown in FIG. 26. As detailed above, the joint 300 and thus, the tool assembly 600 (FIG. 1) are coupled to the outer tube 270 such that the joint 300 and the tool assembly 600 cooperate with rotation of the roll housing 520 about the longitudinal axis A-A. The roll nut 550 also includes a landing 556 opposite the keyway 554.

Continuing to refer to FIGS. 22, 24, and 26, the locking mechanism 560 engages the locking disc 540 to secure the roll housing 520 in fixed rotational orientation relative to the connector 220. In particular, the locking disc 540 defines a plurality of lock cutouts 542 that are configured to receive a locking member 562 of the locking mechanism 560 as described in greater detail below to retain the roll housing 520 in one of a plurality of fixed positions in relation to the connector 220. As shown best in FIG. 22, the lock cutouts 542 are spaced radially about the locking disc 540. It is envisioned that the locking disc 540 may define any number of lock cutouts 542 which may be arranged in any suitable configuration. For example, the lock cutouts 542 may be arranged in set intervals, uniformly or randomly spaced. In addition, the lock cutouts 542 may be formed to extend entirely around the locking disc 540 to permit locking of the roll housing 520 in any three-hundred sixty degree (360°) orientation about the connector 220.

Figure 28:
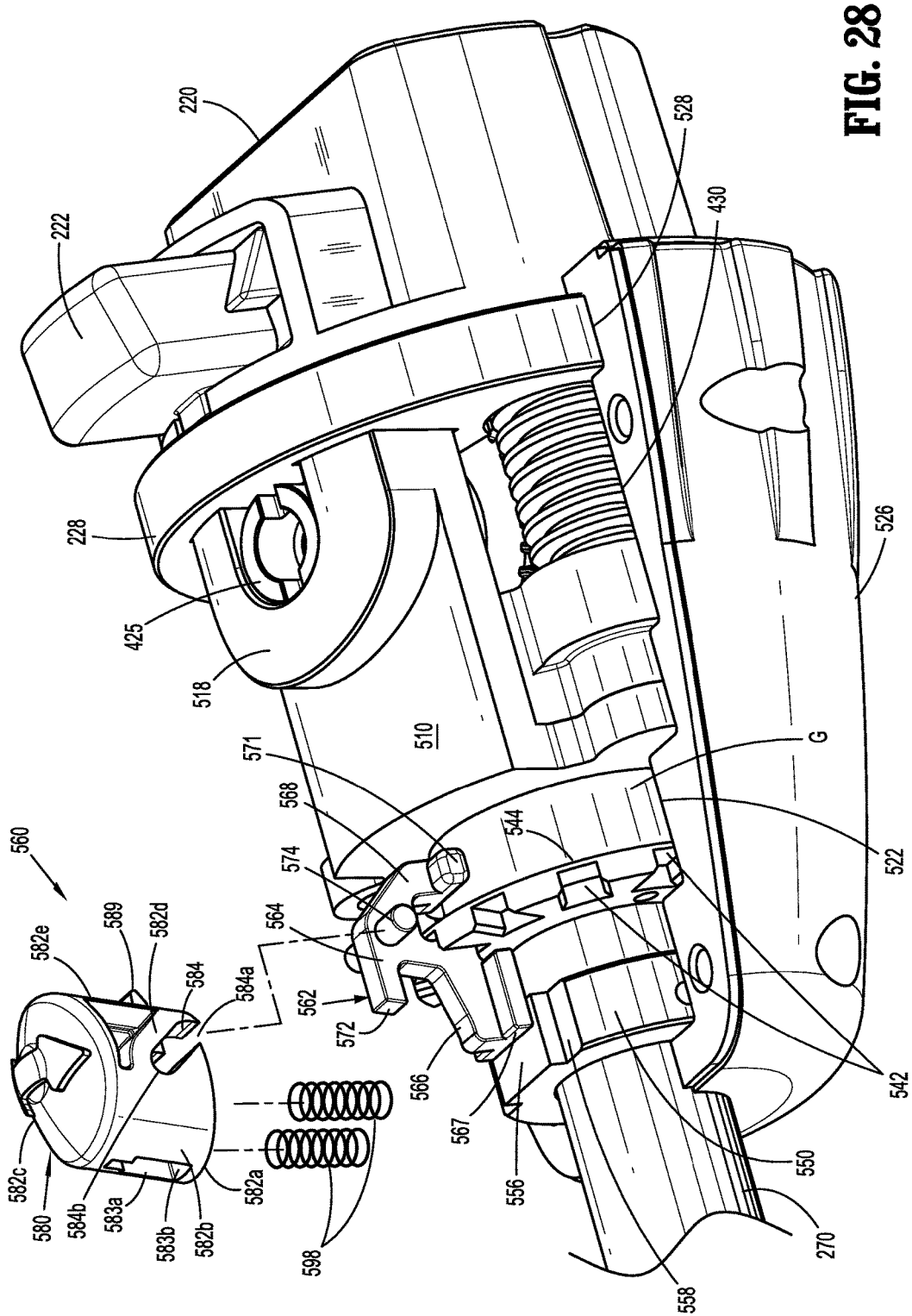
FIG. 28 is a perspective view of the proximal portion of the adapter of FIG. 22 with a first housing shell removed and a button separated from over a locking member.

With additional reference to FIG. 28, the locking mechanism 560 includes the locking member 562, a button 580, and biasing members 598. The locking member 562 includes a lock body 564, a distal leg 566, and a proximal leg 568. The lock body 564 includes a finger 572 that extends over the distal leg 566 and bosses 574 that extend from sides of the lock body 564. The distal leg 566 includes a stop 567 and a lock 569. The stop 567 slides along the landing 556 of the roll nut 550 and forms a T-shape with the distal leg 566. The stop 567 has a width greater than the width of the lock cutouts 542 such that the stop 567 prevents the distal leg 566 from passing entirely through the lock cutouts 542. Additionally or alternatively, the lock 569 may engage a back plate 544 of the locking disc 540 to prevent the distal leg 566 from passing entirely through the lock cutouts 542. The lock 569 is sized and dimensioned to be positioned within a respective one of the lock cutouts 542 when the locking member 562 is in a locked position to prevent rotation of the roll housing 520 relative to the connector 220. The lock 156 extends proximally from the distal leg 566 and is configured such that when the lock 156 is positioned in a respective one of the lock cutouts 542, the stop 567 abuts the locking disc 540. The proximal leg 568 includes a foot 571 that is positioned within the gap "G" defined by the stop 515 of the roll body 510. The distal leg 566 and the proximal leg 568 define a void 574 therebetween that is sized and dimensioned to allow the locking disc 540 to rotate within the void 574 when the locking member 562 is in an unlocked position as shown in FIG. 26.

The button 580 has a button body 582 that defines blind holes (not shown), an opening 583, and camming slots 584. The opening 583 extends inward from a bottom surface 582a of the button body 582 to define a distal opening 583a in a distal surface 582b of the body 582. The distal opening 583a includes a shelf 583b opposite the bottom surface 582a of the button body 582. The blind holes extend substantially vertically from the bottom surface 582a of the button body 582 on either side of the opening 583 in a direction orthogonal to a plane defined by the bottom surface 582a. The blind holes may be substantially cylindrical and are sized to receive the biasing members 598.

The camming slots 584 pass entirely through side surfaces 582d of the button body 582. The camming slots 584 extend from a first end 584a of the button body 582 adjacent the bottom surface 582a of the button body 582 and a proximal surface 582e of the button body 582 to a second end 584b of the button body 582 adjacent the distal surface 582b and a top surface 582c of the button body 582 such that the cam slots 584 are inclined distally upward when the button 580 is viewed in profile. The camming slots 584 are in communication with the opening 583 and configured to receive the bosses 574 of the locking member 562 such that vertical movement of the button 580 (i.e., movement substantially towards and away from the longitudinal axis A-A) affects longitudinal translation of the locking member 562 as described in detail below.

The locking mechanism 560 is disposed in a channel 521 defined in the roll housing 520. The locking mechanism 560 is positioned on the connector 220 adjacent the locking disc 540. In a locked position of the locking mechanism 560, the lock 569 is disposed within one of the lock cutouts 542 defined in the locking disc 540 to rotatably fix the orientation of the roll housing 520 relative to the connector 220. The button 580 is positioned radially outward of the locking member 562 such that the lock body 564 of the locking member 562 is disposed within the opening 583 of the button 580. When the lock body 564 is disposed within the opening 583, the bosses 574 of the locking member 562 are slidingly received within the cam slots 584. In addition, the biasing members 598 are received within the blind holes to urge the button 580 away from the locking member 562. In this position, the locking member 562, due to engagement with the portion of the button 580 defining the cam slots 584, is urged proximally to the locked position. The biasing members 598 are supported on ledges 568 of the roll nut 550 which are adjacent the landing 556 to bias the button 580 away from the locking member 562. However, it is contemplated that the biasing members 598 may be supported by and be slidable along a top surface of the stop 567.

The finger 572 of the locking member 562 extends distally within the opening 583 of the button 580 such that the finger 572 is positioned over the shelf 583b of the button 580 to retain the button 580 within the channel 521 of the roll housing 520. In addition, the proximal surface 581e of the button 580 can include a retention hook 589 that extends proximally from the proximal surface 581e of the button 580 into engagement with the roll housing 520 to retain the button 580 within the channel 521.

As shown in FIGS. 22 and 28, in the locked position of the locking mechanism 560, the button 580 is urged upwardly by the biasing members 598 such that the locking member 562 is cammed by the bosses 574 to a proximal position. In the proximal position, the lock 569 is positioned within a lock cutout 542 of the locking disc 540 to prevent rotation of the roll housing 520 in relation to the connector 220.

As shown in FIG. 26, to transition the lock mechanism 560 to the unlocked position, the button 580 is depressed within the channel 521 of the roll housing 520 against the bias members 598. As the button 580 is depressed, the button 580 is confined to substantially vertical movement (movement towards and away from the longitudinal axis A-A) within the channel 521 of the roll housing 520. As the button 580 is depressed, the bosses 574 slide within the cam slots 584 to affect distal longitudinal movement of the locking member 562 relative to the roll housing 520. Specifically, walls defining the cam slots 584 engage the bosses 574 to translate the locking member 562 in a direction substantially parallel to the longitudinal axis A-A. As the locking member 562 moves distally relative to the button 580, the lock 569 moves from within a cutout 542 to a position distal of the locking disc 540, and thus out of the lock cutout 542. In this position, the roll housing 520 is free to rotate about the connector 220. As the locking member 564 moves distally, the foot 571 of the proximal leg 568 slides within the gap "G" defined by the spacer 515 and may abut the locking disc 540 to limit distal movement of the locking member 564. In embodiments, contact between the foot 571 of the locking member 564 and the locking disc 540 may provide tactile feedback to a clinician that the button 580 is fully depressed and/or that the locking mechanism 560 is in the unlocked position. In addition, when the button 580 is fully depressed, the lock body 564 of the locking member 562 may engage a roof 583c of the opening 583 to limit depression of the button 580 and/or distal movement of the locking member 564.

Continuing to refer to FIG. 26, with the locking mechanism 560 in the unlocked position, the roll housing 520 is rotatable about the connector 220. Rotation of the roll housing 520 also rotates the outer tube 270 about the longitudinal axis A-A through the engagement of the roll nut 550 with the roll housing 520.

It will be appreciated that when the roll housing 520 is rotated relative to the connector 220 with the lock cutouts 542 misaligned with the lock 569 and the button 580 is released, the lock 569 will abut the locking disc 540 until the lock 569 is aligned with one of the lock cutouts 542. When the lock 569 is aligned with one of the lock cutouts 542, the biasing members 598 will urge the button 580 away from the longitudinal axis A-A and affect proximal movement of the locking member 562 such that the lock 569 will slide into the aligned lock cutout 542. When the lock 569 slides into the aligned lock cutout 542, the stop 567 may contact the locking disc 540 to provide audible indicia (a "click") that the roll housing 520 is rotationally secured to the connector 220.

While rotation of the roll housing 520 about the connector 220 is detailed above, it is contemplated that the connector 220 may be rotated within the roll housing 520 such that the tool assembly 600 is repositionable relative to the handle 100 with the tool assembly 600 remaining substantially stationary within a surgical site.

Any of the components described herein may be fabricated from either metals, plastics, resins, composites or the like taking into consideration strength, durability, wearability, weight, resistance to corrosion, ease of manufacturing, cost of manufacturing, and the like.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A joint assembly comprising:
    a proximal joint housing defining a first longitudinal axis and including a first hinge positioned at a distal portion of the proximal joint housing;
    a first ring pivotally coupled to the first hinge about a first pivot axis orthogonal to and intersecting the first longitudinal axis;
    a joint cover having a first cover portion and a second cover portion, the first cover portion pivotally coupled to the first hinge about a second pivot axis orthogonal to and intersecting the first pivot axis and the first longitudinal axis, the first and second pivot axes intersecting the first longitudinal axis at a first joint center;
    a second ring pivotally coupled to the second cover portion of the joint cover about a third pivot axis;
    a second hinge pivotally coupled to the second ring about a fourth pivot axis orthogonal to the third pivot axis, the third and fourth pivot axes intersecting at a second joint center spaced from the first joint center, a cover axis of the joint cover defined between the first and second joint centers; and
    a biasing mechanism engaged with the first ring and the joint cover to bias the first ring and the first cover portion in a direction parallel to the first longitudinal axis, and to bias the joint cover towards an aligned configuration in which the cover axis is aligned with the first longitudinal axis.

2. The joint assembly according to claim 1, wherein the biasing mechanism includes a pair of inner biasing bars and a pair of outer biasing bars, the pair of inner biasing bars engaged with the first cover portion of the joint cover and the pair of outer biasing bars engaged with the first ring.

3. The joint assembly according to claim 2, wherein each of the inner and outer biasing bars of the pairs of inner and outer biasing bars extends longitudinally and is translatable in a direction parallel to the first longitudinal axis.

4. The joint assembly according to claim 3, wherein each of the inner and outer biasing bars of the pairs of inner and outer biasing bars is operably associated with a respective biasing member that is configured to urge the associated biasing bar through the first hinge.

5. The joint assembly according to claim 4, wherein in an aligned configuration of the second hinge, a second longitudinal axis is aligned with the cover axis and the first longitudinal axis, the second longitudinal axis passing through the second joint center and extending through the center of the second hinge.

6. The joint assembly according to claim 5, wherein in a first articulated configuration of the joint assembly, the second longitudinal axis is articulated relative to the cover axis with the joint cover in the aligned configuration and in a second articulated configuration of the joint assembly, the second longitudinal axis is articulated relative to the cover axis and the cover axis is articulated relative to the first longitudinal axis.

7. The joint assembly according to claim 6, wherein the biasing mechanism is configured to maintain the joint assembly in the first articulated configuration until the second longitudinal axis is articulated to a maximum angle of articulation relative to the cover axis.

8. The joint assembly according to claim 7, wherein the maximum angle of articulation is in a range of 15° to 45°.

9. The joint assembly according to claim 1, further comprising:
    a first drive shaft extending through the first hinge;
    a joint body having a first body portion and a second body portion, the first body portion being rotatably disposed within the first cover portion and rotatably and pivotally coupled to the first drive shaft, the second body portion being rotatably disposed within the second cover portion; and
    a second drive shaft extending through the second hinge, the second drive shaft rotatably and pivotally coupled to the second body portion.

10. The joint assembly according to claim 9, wherein a drive ball of the first drive shaft is disposed within the first body portion.

11. The joint assembly according to claim 10, wherein the first drive shaft is rotatably disposed along the first longitudinal axis, the drive ball defining a center channel orthogonal to the first longitudinal axis and arced slots in a plane aligned with the first longitudinal axis and bisecting the center channel.

12. The joint assembly according to claim 11, further comprising:
    a center pin disposed within the center channel and defining a pin opening orthogonal to a central longitudinal axis of the center pin; and
    a shaft pin disposed within the pin opening and the arced slots to rotatably couple the joint body to the first drive shaft.

13. The joint assembly according to claim 12, wherein the arced slots and the shaft pin cooperate to limit articulation between the first drive shaft and the joint body.

14. The joint assembly according to claim 9, wherein the second drive shaft further includes a receiver, the receiver being rotatably disposed within the second cover portion and receiving the second body portion.

15. The joint assembly according to claim 14, wherein the cover axis passes through the first and second joint centers, the second body portion defining a center channel orthogonal to the cover axis and arced slots in a plane aligned with the cover axis and bisecting the center channel.

16. The joint assembly according to claim 15, wherein the joint body is rotatable along the cover axis.

17. The joint assembly according to claim 15, further comprising:
   a center pin disposed within the center channel and defining a pin opening that is orthogonal to a central longitudinal axis of the center pin; and
   a shaft pin disposed within the pin opening and the arced slots to rotatably couple the joint body to the second drive shaft.

18. The joint assembly according to claim 17, wherein the arced slots and the shaft pin cooperate to limit articulation between the joint body and the second drive shaft.

19. An adapter comprising:
   a proximal portion configured to couple to a handle;
   an elongate portion extending from the proximal portion and defining a first longitudinal axis; and
   a distal portion supported by the elongate portion and configured to releasably couple a tool assembly to the handle, the distal portion including a joint assembly having:
      a first hinge disposed along the first longitudinal axis and positioned at a distal end of the elongate portion;
      a first ring pivotally coupled to the first hinge about a first pivot axis orthogonal to and intersecting the first longitudinal axis;
      a joint cover having a first cover portion and a second cover portion, the first cover portion pivotally coupled to the first hinge about a second pivot axis orthogonal to and intersecting the first pivot axis and the first longitudinal axis, the first and second pivot axes intersecting the first longitudinal axis at a first joint center; a second ring pivotally coupled to the second cover portion of the joint cover about a third pivot axis;
      a second hinge pivotally coupled to the second ring about a fourth pivot axis orthogonal to the third pivot axis, the third and fourth pivot axes intersecting at a second joint center spaced from the first joint center, a cover axis of the joint cover defined between the first and second joint centers; and
   a biasing mechanism engaged with the first ring and the joint cover to bias the first ring and the first cover portion in a direction parallel to the first longitudinal axis, and to bias the joint cover towards an aligned configuration in which the cover axis is aligned with the first longitudinal axis.

* * * * *